United States Patent [19]

Kahan et al.

[11] Patent Number: 5,071,843
[45] Date of Patent: Dec. 10, 1991

[54] COMBINATION OF 2-SUBSTITUTED CARBAPENEMS WITH DIPEPTIDASE INHIBITORS

[75] Inventors: Frederick M. Kahan, Scotch Plains; Helmut Kropp, Kenilworth, both of N.J.

[73] Assignee: Merck & Co., Inc., Rahway, N.J.

[21] Appl. No.: 681,486

[22] Filed: Apr. 3, 1991

Related U.S. Application Data

[63] Continuation of Ser. No. 471,678, Jan. 25, 1990, abandoned, which is a continuation of Ser. No. 384,845, Jul. 24, 1989, abandoned, which is a continuation of Ser. No. 880,339, Jun. 25, 1986, abandoned, which is a continuation of Ser. No. 605,343, Apr. 30, 1984, abandoned, which is a continuation-in-part of Ser. No. 340,152, Jan. 18, 1982, abandoned, which is a continuation-in-part of Ser. No. 291,711, Aug. 10, 1981, Pat. No. 4,539,208, which is a continuation-in-part of Ser. No. 187,929, Sep. 17, 1980, abandoned, which is a continuation-in-part of Ser. No. 50,232, Jun. 22, 1979, abandoned, which is a continuation-in-part of Ser. No. 927,213, Jul. 24, 1978, abandoned.

[51] Int. Cl.$^5$ .................... A61K 31/16; A61K 21/22; A61K 31/195; A61K 31/215; A61K 31/395
[52] U.S. Cl. .................... 514/210; 514/531; 514/549; 514/563; 514/629
[58] Field of Search ............... 514/210, 531, 549, 563, 514/629

[56] References Cited

U.S. PATENT DOCUMENTS 4,539,208 9/1985 Kahan et al. .................... 514/195
4,552,873 11/1985 Miyadera et al. .................... 514/210

FOREIGN PATENT DOCUMENTS 0007614 2/1979 European Pat. Off. .
0028778 5/1981 European Pat. Off. .
2013674 8/1979 United Kingdom .
2042520 9/1980 United Kingdom .

OTHER PUBLICATIONS

Journal of Antibiotics, vol. 36, No. 8, Aug. (1983) pp. 1034–1039.
Drugs of the Future, vol. 10, No. 12 (1985) pp. 989–992.

Primary Examiner—Frederick E. Waddell
Assistant Examiner—Raymond J. Henley, III
Attorney, Agent, or Firm—Frank P. Grassler; Robert J. North; Hesna J. Pfeiffer

[57] ABSTRACT

A combination of a carbapenem of the formula:

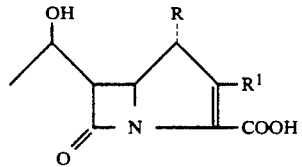

where R is H or $CH_3$ and $R^1$ is

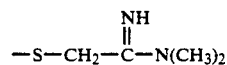

or

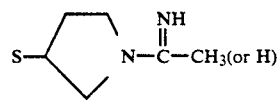

with a renal dipeptidase inhibitor is disclosed.

5 Claims, No Drawings

COMBINATION OF 2-SUBSTITUTED CARBAPENEMS WITH DIPEPTIDASE INHIBITORS

CROSS REFERENCE TO RELATED APPLICATIONS

This is a continuation of application Ser. No. 07/471,678, filed Jan. 25, 1990, now abandoned, which is a continuation of application Ser. No. 07/384,845, filed July 24, 1989, now abandoned, which is a continuation of application Ser. No. 06/880,339, filed June 25, 1986, now abandoned, which is a continuation of application Ser. No. 06/605,343, filed Apr. 30, 1984, now abandoned, which is a continuation-in-part of application Ser. No. 06/340,152, filed Jan. 18, 1982, now abandoned, which is a continuation-in-part of application Ser. No. 06/291,711, filed Aug. 10, 1981, now U.S. Pat. No. 4,539,208, which is a continuation-in-part of application Ser. No. 06/187,929, filed Sept. 17, 1980, now abandoned, which is a continuation-in-part of application Ser. No. 06/050,232 filed June 22, 1979, now abandoned, which is a continuation-in-part of application Ser. No. 05/927,213, filed July 24, 1978, now abandoned.

SUMMARY OF THE INVENTION

The compounds 2-substituted carbapenems are those having the following structure (described as the free acid, but also including easily removable or pharmaceutically acceptable salt or ester groups):

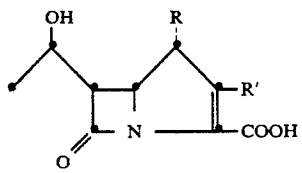

wherein R is hydrogen or methyl; and R' is

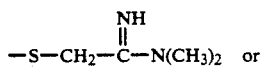

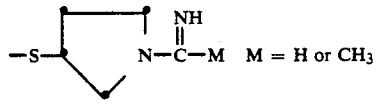

The carbapenem compounds have a high level of antibacterial activity, but are subject to extensive metabolism by mammalian species.

The kidney was identified as the primary site of metabolism, and an enzyme was purified from renal extracts which catalyzed the inactivation of thienamycin by hydrolysis of the β-lactam. By such criteria as cytological localization, substrate specificity and susceptibility to enzyme inhibitors, this enzyme is very similar if not identical to a widely studied renal dipeptidase (E.C. 3.4.13.11), also referred to in the literature as "dehydropeptidase - I".

We have now found that these carbapenems can be combined with a class of chemical compounds which are dipeptidase inhibitors, and which selectively inhibit the metabolism of the dipeptidase (E.C. 3.4.13.11). These chemical compounds are Z-2-acylamino-3-monosubstituted propenoates having the following formula:

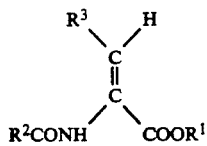

wherein $R^2$ and $R^3$ are hydrocarbon radicals in the range respectively of 3-10 and 1-15 carbon atoms. In either of these hydrocarbon radicals $R^2$ and $R^3$, up to 6 hydrogens may be replaced by halogens, or a non-terminal methylene may be replaced by oxygen or sulfur, including oxidized forms of the latter.

A terminal hydrogen in $R^3$ can also be replaced by a hydroxyl or thiol group, which may be acylated, such as with an alkanoyl acid of 1-8 carbon atoms, or carbamoylated, including alkyl and dialkyl carbamate derivatives; or the hydrogen can be replaced by an amino group, which may be derivatized as in an acylamino, ureido, amidino, guanidino, or alkyl or substituted alkyl amino group, including quaternary nitrogen groupings; or, alternatively, there may be replacement by acid groups such as carboxylic, phosphonic or sulfonic acid groups or esters or amides thereof, as well as cyano; or combinations thereof, such as a terminal amino acid grouping.

$R^2$ is preferably a branched alkyl or cycloalkyl radical ($C_{3-10}$), with a limitation that the carbon adjacent to the carbonyl cannot be tertiary. $R^2$ cannot be phenyl or straight chain loweralkyl of 1-4 carbon atoms, where $R^3$ is straight chain lower alkyl of 1-4 carbon atoms. $R^1$ is hydrogen, loweralkyl ($C_{1-6}$) or dialkylaminoalkyl (e.g., $-CH_2CH_2N(C_2H_5)_2$, $-CH_2CH(CH_3)N(CH_3)_2$.

Some of the compounds with formula II above have asymmetric forms. Racemic Z-2-(2,2-dimethylcyclopropanecarboxamido)-2-octenoic acid has been resolved. The activity resides in the dextrorotatory isomer, which has the S-configuration.

Within the definition of $R^2$, the following sub-groups are included:

$$-R^4 \qquad \text{II A}$$

wherein $R^4$ is a straight, branched, or cyclic hydrocarbon radical of 3-10 carbon atoms which may be substituted as specified above in the definition of $R^2$;

$$-R^5R^6 \qquad \text{II B}$$

wherein $R^5$ is cycloalkyl of 3-6 carbon atoms and $R^6$ is either 1 or 2 alkyl substituents which may be joined to form another ring on the cycloalkyl group, or $R^5$ and $R^6$ may be substituted as specified above in the definition of $R^2$;

$$-R^7R^8 \qquad \text{II C}$$

wherein $R^7$ is an alkylene group of 1-3 carbon atoms and $R^8$ is cycloalkyl of 3-6 carbon atoms which may be substituted as specified above in the definitions of $R^2$ and $R^3$;

within these sub-groups, the following specific compounds are included:

II A: Z-2-isovaleramido-2-pentenoic acid; methyl Z-2-isovaleramido-2-butenoate; Z-2-isovaleramido-2- butenoic acid; Z-2-benzamido-2-butenoic acid; Z-2-(3,5,5-trimethylhexanamido)-2-butenoic acid; Z-2-cyclobutanecarboxamido-2-butenoic acid; Z-2-cyclopropanecarboxamido-2-butenoic acid; Z-2-cyclopropanecarboxamido-2-pentenoic acid; Z-2-(3-methylvaleramido)-2-butenoic acid; Z-2-cycloheptanecarboxamido-2-butenoic acid; Z-2-nonanamido-2-butenoic acid; Z-2-cyclohexanecarboxamido-2-butenoic acid; Z-2-(4-methylvaleramido)-2-butenoic acid; Z-2-t-butylacetamido-2-butenoic acid; Z-2-octanamido-2-butenoic acid; Z-2-butyramido-2-butenoic acid; Z-2-valeramido-2-butenoic acid; Z-2-valeramido-2-pentenoic acid; Z-2-cyclopentanecarboxamido-2-butenoic acid; Z-2-(6-methylheptanamido)-2-butenoic acid; Z-2-hexanamido-2-butenoic acid; Z-2-(3,7-dimethyloctanamido)-2-butenoic acid; Z-2-(3,7-dimethyl-6-octenamido)-2-butenoic acid; Z-2-(5-chlorovaleramido)-2-butenoic acid; Z-2-(3-chlorobenzoylamido)-2-butenoic acid; Z-2-(2-chlorobenzamido)-2-butenoic acid; Z-2-nonanamido-2-butenoic acid; Z-2-(6-bromohexanamido)-2-butenoic acid; Z-2-(3,3-dimethylpropenamido)-2-butenoic acid; Z-2-benzamido-2-cinnamic acid; Z-2-benzamido-2-pentenoic acid; Z-2-benzamido-5-methoxy-2-pentenoic acid; Z-2-benzamido-2-hexenedioic acid; Z-2-isovaleramido-2-octenoic acid; Z-2-isovaleramido-2-cinnamic acid; Z-2-isovaleramido-2-hexenedioic acid; Z-2-cyclopropanecarboxamido-2-cinnamic acid; Z-2-cyclopropanecarboxamido-2-hexenedioic acid; Z-2-(5-methoxy-3-methylvaleramido)-2-butenoic acid; Z-2-ethylthioacetamido-2-butenoic acid; Z-2-(2,2-dichlorocyclopropanecarboxamido)-2-butenoic acid; Z-2-(2-ethylhexanamido)-2-butenoic acid; Z-2-di-n-propylacetamido-2-butenoic acid;

II B: Z-2-(2,2-dimethylcyclopropanecarboxamido)-2-butenoic acid; (+)-Z-2-(2,2-dimethylcyclopropanecarboxamido)-2-butenoic acid; Z-2-(2,2-dimethylcyclopropanecarboxamido)-2-pentenoic acid; Z-2-(2,2-dimethylcyclopropanecarboxamido)-2-octenoic acid; Z-2-(2,2-dimethylcyclopropanecarboxamido)-2-hexenoic acid; Z-2-(2,2-dimethylcyclopropanecarboxamido)-2-cinnamic acid; Z-2-(2,2-dimethylcyclopropanecarboxamido)-5-methoxy-2-pentenoic acid; Z-2-(2,2-dimethylcyclopropanecarboxamido)-4,4,4-trifluoro-2-butenoic acid; Z-2-(2,2-dimethylcyclopropanecarboxamido)-3-(2-chlorophenyl)propenoic acid; Z-2-(2,2-dimethylcyclopropanecarboxamido)-2-hexenedioic acid; Z-2-(2-ethylcyclopropanecarboxamido)-2-butenoic acid; Z-2-(2,2-diethylcyclopropanecarboxamido)-2-butenoic acid; Z-2-(2,2-diethylcyclopropanecarboxamido)-2-pentenoic acid; Z-2-(2-isopropyl-2-methylcyclopropanecarboxamido)-2-butenoic acid; Z-2-(2-methylcyclohexanecarboxamido)-2-butenoic acid; Z-5-cyano-2-(2,2-dimethylcyclopropanecarboxamido)-2-pentenoic acid; Z-5-(N,N-dimethylcarbamoyl)-2-(2,2-dimethylcyclopropanecarboxamido)-2-pentenoic acid; Z-2-(2,2-dimethylcyclopropanecarboxamido)-5-methanesulfonyl-2-pentenoic acid; Z-2-(2,2-dimethylcyclopropanecarboxamido)-5-ethoxycarbonyl-2-pentenoic acid; Z-2-(2-methylcyclopropanecarboxamido)-2-butenoic acid; methyl Z-2-(2,2-dimethylcyclopropanecarboxamido)-2-butenoate; ethyl Z-2-(2,2-dimethylcyclopropanecarboxamido)-2-butenoate; 2-dimethylaminoethyl ester of Z-2-(2,2-dimethylcyclopropanecarboxamido)-2-butenoic acid; 3-diethylaminopropyl ester of Z-2-(2,2-dimethylcyclopropanecarboxamido)-2-pentenoic acid; Z-2-(2,3-dimethylcyclopropanecarboxamido)-2-butenoic acid; Z-2-(3,3-dimethylcyclobutanecarboxamido)-2-butenoic acid; Z-2-(2-spirocyclopentanecarboxamido)-2-butenoic acid; Z-2-(2-t-butyl-3,3-dimethylcyclopropanecarboxamido)-2-butenoic acid; Z-2-(2,2-dimethylcyclopropanecarboxamido)-4-methyl-2-pentenoic acid; Z-2-(2-t-butylcyclopropanecarboxamido)-2-butenoic acid; Z-2-(2-phenylcyclopropanecarboxamido)-2-butenoic acid; Z-3-cyclohexyl-2-(2,2-dimethylcyclopropanecarboxamido)-propenoic acid; Z-5-carboxy-5-(2,2-dimethylcyclopropanecarboxamido)-4-pentenamidine; Z-5-dimethylamino-2-(2,2-dimethylcyclopropanecarboxamido)-2-pentenoic acid; Z-3-cyclopropyl-2-(2,2-dimethylcyclopropanecarboxamido)propenoic acid; Z-2-(2,2-dimethylcyclopropanecarboxamido)--2,5-hexadienoic acid; Z-2-(2,2-dimethylcyclopropanecarboxamido)-4-phenyl-2-butenoic acid; Z-2-(2,2-dimethylcyclopropanecarboxamido)-6-mercapto-2-hexenoic acid; Z-2-(2,2-dimethylcyclopropanecarboxamido)-5-methylthio-2-pentenoic acid; Z-2-(2,2-dimethylcyclopropanecarboxamido)-5-phosphono-2-pentenoic acid; Z-2-(2,2-dimethylcyclopropanecarboxamido)-2-heptenoic acid; Z-2-(2,2-dimethylcyclopropanecarboxamido)-5-phenyl-2-pentenoic acid; Z-2-(2,2-dimethylcyclopropanecarboxamido)-2-nonenoic acid; Z-2-(2,2-dimethylcyclopropanecarboxamido)-2-decenoic acid; Z-2-(2,2-dimethylcyclopropanecarboxamido)-2-tridecenoic acid; Z-2-(2,2-dimethylcyclopropanecarboxamido)-6-methoxy-2-hexenoic acid (and 5-methoxy-2-pentenoic acid); Z-2-(2,2-dimethylcyclopropanecarboxamido)-6-methyl-2-heptenoic acid; Z-4-cyclohexyl-2-(2,2-dimethylcyclopropanecarboxamido)-2-butenoic acid;

II C: Z-2-cyclobutylacetamido-2-butenoic acid; Z-2-cyclopentylacetamido-2-butenoic acid; Z-2-cyclohexylacetamido-2-butenoic acid; Z-2-(4-cyclohexylbutyramido)-2-butenoic acid; Z-2-cyclopropylacetamido-2-butenoic acid; Z-2-cyclopropylacetamido-2-pentenoic acid; Z-2-(3-cyclopentylpropionamido)-2-butenoic acid; Z-2-(3-cyclohexylpropionamido)-2-butenoic acid; Z-2-(4-(2-thienyl)-butyramido)-2-butenoic acid; Z-2-(4-phenylbutyramido)-2-butenoic (D,L-α-lipoamido)-2-pentenoic acid; Z-2-(D,L-α-lipoamido)-2-cinnamic acid; Z-2-(3-(2-tetrahydrofuryl)-propionamido)-2-butenoic acid.

Particularly preferred substituents within the definition of R² above include the 2,2-dimethylcyclopropyl and the 2,2-dichlorocyclopropyl groups.

Within the definition of R³, particularly preferred groups of compounds include n-alkyl (1–9 carbons) and n-alkyl (1–9 carbons) having a terminal substituent which is a quaternary nitrogen, amine derivative, or amino acid derived group.

By the term "quaternary nitrogen" is meant a tetrasubstituted or heteroaromatic nitrogen which is positively charged. An ammonium moiety, substituted with hydrocarbon groups having 1–7 carbon atoms, which can be the same or different, is signified.

By the term "amino derivative" is meant a group such as amino, acylamino, ureido, amidino, guanidino and alkyl (1–7 carbon atoms) derivatives thereof.

By the term "amino acid derived group" is meant a moiety such as cysteinyl (—SCH₂CH(NH₂)COOH) or sarcosyl (—N(CH₃)CH₂COOH) in which a hydrogen joined to O, N or S of known amino acids is replaced.

Particularly preferred compounds from the most preferred groups of substituents of R² and R are those wherein R² is 2,2-dimethylcyclopropyl or 2,2-dichlorocyclopropyl, and R³ is a hydrocarbon chain of 3 to 7 carbon atoms without a terminal substituent, or having a terminal substituent which is trimethylammonium, amidino, guanidino, or 2-amino-2-carboxyethylthio. Names of specific examples of these include:

Z-2-(2,2-dimethylcyclopropanecarboxamido)-8-trimethylammonium hydroxide-2-octenoic acid inner salt;

Z-2-(2,2-dichlorocyclopropanecarboxamido)-8-trimethylammonium hydroxide-2-octenoic acid inner salt;

Z-2-(2,2-dimethylcyclopropanecarboxamido)-8-formamidino-2-octenoic acid;

Z-2-(2,2-dimethylcyclopropanecarboxamido)-8-guanidino-2-octenoic acid;

Z-2-(2,2-dimethylcyclopropanecarboxamido)-8-ureido-2-octenoic acid;

Z-8-(L-2-amino-2-carboxyethylthio)-2-(2,2-dimethylcyclopropanecarboxamido)-2-octenoic acid;

Z-2-(2,2-dimethylcyclopropanecarboxamido)-2-octenoic acid (racemic and dextrorotatory forms);

Z-2-(2,2-dichlorocyclopropanecarboxamido)-2-octenoic acid;

7-(L-2-amino-2-carboxyethylthio)-2-(2,2-dimethylcyclopropanecarboxamido)-2-heptenoic acid; and 6-(L-2-amino-2-carboxyethylthio)-2-(2,2-dimethylcyclopropanecarboxamido)-2-hexenoic acid.

The Z configuration (J. E. Blackwood et al., *J. Am. Chem. Soc.*, 90, p. 509 (1968)) is assigned to the above compounds on the basis of their NMR spectra by analogy with the work of A. Srinavasan et al. [Tetrahedron Lett., 891 (1976)].

Although these compounds of Formula II, when $R^1$ is H, are described and named as the free acids, it will be apparent to one skilled in the art that various pharmaceutically acceptable derivatives such as alkali and alkaline earth metal, ammonium, or amine salts, or the like can be employed as equivalents thereto. Salts such as the sodium, potassium, calcium, or tetramethylammonium salts are suitable.

Some of the compounds of Formula II are novel compounds which are claimed in a copending U.S. application, U.S. Ser. No. 927,212, filed on July 24, 1978, now abandoned; and in U.S. Ser. No. 050,233, filed June 22, 1979, now abandoned; and in U.S. Ser. No. 188,178, filed Sept. 17, 1980, and which do not form part of this invention.

As mentioned above, the carbapenem compound is used in combination with the dipeptidase inhibitor.

METHODS OF TESTING AND USING THE INVENTION

Disposition studies with thienamycin, its natural analogs and its semi-synthetic derivatives have revealed a major metabolic degradation pathway of elimination in the various species examined (mouse, rat, dog, chimpanzee, Rhesus monkey). The extent of metabolism is reflected in low urinary recovery and short plasma half-lives. The nature of this degradation was demonstrated to be lactam cleavage by the renal dipeptidase (E.C.3.4.13.11), described first by Bergmann, M. and Schleich, H., *Z. Physiol. Chem.*, 205 65 (1932); see also Greenstein, J.P., *Advances in Enzymology*, Vol. VIII, Wiley-Interscience, (1948), New York, and Campbell, B. J.; Lin, Y-C., Davis, R. V. and Ballew, E., "The Purification and Properties of Particulate Renal Dipeptidase", *Biochim. Biophys. Acta.*, 118, 371 (1966).

In order to demonstrate the ability of the compounds of Formula II to suppress the action of the renal dipeptidase enzyme, an in vitro screen procedure was followed. This measured the ability of compounds to inhibit hydrolysis of glycyldehydrophenylalanine (GDP) by a solubilized preparation of dipeptidase isolated from hog kidneys. The procedure is as follows: to a 1 ml. system containing 50 mM "MOPS" (3-(N-morpholino)-propanesulfonic acid) buffer, pH 7.1, is added 5 μg of lyophilized enzyme, and the test compound at a final concentration of 0.1 mM. After a five minute incubation at 37° C., GDP is added to a final concentration of 0.05 mM. Incubation is continued for 10 minutes, at 37° C. and hydrolysis of GDP is measured by the change in optical density with time at 275 nm. Inhibition of the enzyme is gauged by comparison to a standard run containing no inhibitor and is expressed as the inhibitor binding constant, $K_i$. This is the concentration of the inhibitor which achieves 50% inhibition of enzyme.

The substrate GDP is employed in preference to thienamycin in this screen because it has a much higher maximal velocity of hydrolysis by renal dipeptidase, thereby reducing the amount of enzyme required. Both GDP and thienamycin have a similar affinity for renal dipeptidase; furthermore, $K_i$'s of inhibitors tested have been identical for the two substrates.

In addition to this in vitro screen procedure, an in vivo screen was followed to measure the test compound's ability to inhibit metabolism as reflected by increase in urinary recovery of the carbapenems of formula I from the mouse. The procedure involves co-administration of the test compound by the intravenous or subcutaneous route at a dose-rate of 10–100 mg/kg, with 10 mg/kg carbapenem. Carbapenem recovery in the urine over a 4 hour period is then compared with its recovery in a control group to which test compound was not co-administered.

Urinary recovery of carbapenem was measured in all cases with the use of a cylinder or disc diffusion assay, conducted in a manner described in U.S. Pat. No. 3,950,357. This bioassay, with Staphylococcus aureus ATCC 6538 as the test organism, has a useful response range from 0.04 μg/ml to 3.0 μg/ml.

The combination of the inhibitor and the carbapenem can be in the form of a pharmaceutical composition containing the two compounds in a pharmaceutically acceptable carrier. The two can be employed in amounts so that the weight ratio of the penem to inhibitor is 1:3 to 30:1, and preferably 1:1 to 5:1.

The components can also be separately administered. For instance, the carbapenem can be administered intramuscularly or intravenously in amounts of 1–100 mg/kg/day, preferably 1–20 mg/kg/day, or 1–5 mg/kg/dose, in divided dosage forms, e.g., three or four times a day. The inhibitor can be separately administered, orally, intramuscularly, or IV, in amounts of 1–100 mg/kg/day, or preferably 1–30 mg/kg/day, or 1–5 mg/kg/dose in divided dosage forms, e.g., three or four times a day. The amounts of the two components administered during one day ideally are within the ratio limits denoted above.

One preferred dosage regimen and level is the combination of the compound 2-[3S]-1-acetimidoyl-pyrrolidin-3-yl-thio)-6-(1-hydroxyethyl)-carbapen-2-em-3-sodium carboxylate and the crystalline form of 7-(L-amino-2-carboxyethylthio)-2-(2,2-dimethylcyclopropanecarboxamido)-2-heptenoic acid, co-administered in a sterile aqueous IV injection form (sodium salt), at a level of 250 or 500 mg of the penem compound and about 1:1 (weight) of the heptenoic acid, or 250 or 500 mg. This dose can be given to humans (each assumed to weigh about 80 kg.) from 1 to 4 times daily, that is 3.1-25 mg/kg/day of each drug. This carbapenem can also be combined with inhibitor, ±Z-2-(2,2-dimethylcyclopropanecarboxamido)-2-ocetenoic acid and both administered parenterally, at dose levels (estimated for humans at 2-8 mg/kg/dose of the carbapenem and 1-8 mg/kg/dose of the inhibitor, such doses being administered 1-4 times a day.

The components, whether administered separately or together are employed in pharmaceutically acceptable carriers such as conventional vehicles adapted for parenteral administration such as liquid solutions, emulsions or suspensions. The components separately or together, can be dissolved in a vehicle adapted for administration by injection.

Examples which illustrate this invention follow.

SECTION 1. EXAMPLES ILLUSTRATING ACTIVITY

Example 1

In Vitro Test Data

A 1 ml. system of 50 mM "MOPS" buffer, pH 7.1, is used. To this is added 5 µg of the pig renal enzyme and an amount of the test compound to bring its final concentration to 0.1 mM. After a five minute incubation at 37° C., an amount of GDP is added to bring its final concentration to 0.05 mM. The system is again incubated for 10 minutes, at 37° C. Hydrolysis of GDP is measured by its change in optical density with time at 275 nm. Inhibition of the enzyme is gauged by comparison to a standard run containing no inhibitor and is presented as percent inhibition. The $K_i$ is a constant indicating the concentration of inhibitor necessary to produce 50% inhibition of enzyme. It is a calculated value obtained from running multiple in vitro assays, as above, at concentrations resulting in inhibition below and above the 50% inhibition point. The results are presented in Table I.

TABLE I $$R^3-C=C-NHCOR^2$$
$$\overset{\phantom{R^3-C=}}{\underset{\phantom{R^3-C}}{|}}\text{COOH}$$

| Compounds Dipeptidase Inhibitor | $R^3$ | $R^2$ | % Inhibition at $10^{-4}$ M | $K_i$ (µM) |
|---|---|---|---|---|
| 1 | $CH_2CH_3$ | cyclopropyl-C(CH₃)₂ (gem-dimethyl) | 98 | 0.18 |
| 2* | $CH_3$ | cyclopropyl-C(CH₃)₂ | 98 | 0.39 |
| 2a* | $CH_3$ | cyclopropyl-C(CH₃)₂ | 100 | 0.12 |
| 2b* | $CH_3$ | cyclopropyl-C(CH₃)₂ | | 19.8 |
| 3 | $CH_3$ | cyclopropyl-CH₃ | 92 | 1.7 |
| 4 | $CH_2CH_3$ | $CH_2-CH(CH_3)_2$ | 87 | 3.2 |
| 5 | $CH_3$ | $-CH_2CH(CH_3)-CH_2C(CH_3)_3$ | 81 | 4.4 |
| 6 | $CH_3$ | 2,2-dimethylcyclopropyl | 83 | 4.6 |
| 7 | $CH_3$ | $CH_2-CH(CH_3)_2$ | 91 | 6 |

TABLE I-continued $$R^3-\overset{*}{C}=\overset{COOH}{\underset{|}{C}}-NHCOR^2$$

| Compounds Dipeptidase Inhibitor | $R^3$ | $R^2$ | % Inhibition at $10^{-4}$ M | $K_i$ ($\mu$M) |
|---|---|---|---|---|
| 8 | CH$_3$ | 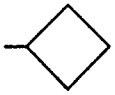 | 80 | 6.2 |
| 9 | CH$_3$ | —CH$_2$—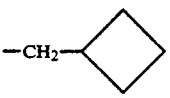 | 83 | 6.6 |
| 10 | CH$_3$ |  | 97 | 9 |
| 11 | CH$_3$ | —CH$_2$—CH—CH$_2$CH$_3$<br>     \|<br>     CH$_3$ | 82 | 10 |
| 12 | —(CH$_2$)$_4$CH$_2$ | 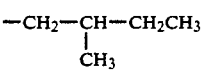 |  | 0.059 |
| 13 | —(CH$_2$)$_5$N$^+$(CH$_3$)$_3$ | 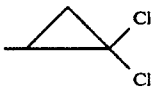 |  | 0.18 |
| 14 | —(CH$_2$)$_5$N$^+$(CH$_3$)$_3$ | 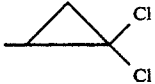 |  | 1.11 |
| 15 | —(CH$_2$)$_5$—NH—$\overset{\overset{CH_3}{\|}}{C}$=NH | 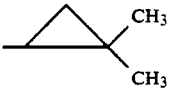 |  | 0.72 |
| 16 | —(CH$_2$)$_5$—NH—$\overset{\overset{NH}{\|\|}}{C}$—N(CH$_3$)$_2$ |  |  | 0.89 |
| 17 | —(CH$_2$)$_4$—S—CH$_2$—$\overset{\overset{H}{\|}}{\underset{\underset{NH_3^+}{\|}}{C}}$—COO$^-$ | 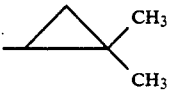 |  | 0.21 |
| 18 | CH$_3$ | —CH$_2$C(CH$_3$)$_3$ | 75 | 20 |
| 19 | CH$_3$ | —(CH$_2$)$_6$CH$_3$ | 72 | 26 |
| 20 | CH$_3$ | —(CH$_2$)$_2$CH$_3$ | 69 | 30 |
| 21 | CH$_3$ | —(CH$_2$)$_3$—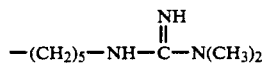 | 68 | 30 |
| 22 | CH$_3$ | —CH$_2$—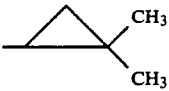 | 64 | 22 |
| 23 | CH$_3$ | (CH$_2$)$_3$CH$_3$ | 64 | 32 |

TABLE I-continued $$R^3-\overset{*}{C}=\overset{COOH}{\underset{|}{C}}-NHCOR^2$$

| Compounds Dipeptidase Inhibitor | $R^3$ | $R^2$ | % Inhibition at $10^{-4}$ M | $K_i$ (μM) |
|---|---|---|---|---|
| 24 | $CH_3$ | cyclopentyl | 59 | 30 |
| 25 | $CH_3$ | $-(CH_2)_4CH(CH_3)_2$ | 57 | |
| 26 | $CH_3$ | $-CH_2CH_2-$cyclopentyl | 56 | |
| 27 | $CH_3$ | $-CH_2CH_2-$cyclohexyl | 54 | |
| 28 | $CH_3$ | $-CH_2-(CH_2)_3CH_3$ | 54 | 39 |
| 29 | $CH_3$ | $-(CH_2)_5CH_3$ | 49 | |
| 30 | $CH_3$ | $-CH(CH_2CH_3)CH_2CH_2CH_3$ | 33 | |
| 31 | $CH_3$ | $-CH(CH_2CH_2CH_3)_2$ | 13 | |
| 32 | $CH_3$ | $-CH(CH_3)_2$ | 31 | |
| 33 | $HOO-CH_2CH_2$ | cyclopropyl | 90 | 5 |
| 34 | $CH_3$ | $-CH_2-CH(CH_3)-CH_2CH_2OCH_3$ | 88 | 9 |
| 35 | $CH_3$ | $CH_2CH_2CH_2CH_2CH_2Br$ | 70 | 19 |
| 36 | $CH_3$ | $CH_2CH_2CH_2CH_2Cl$ | 64 | 20 |
| 37 | $CH_3$ | $CH_2CH_2CH_2-$phenyl | 72 | 11 |
| 38 | $CH_3$ | cyclopropyl-$C(CH_3)_3$ | 90 | 6.5 |
| 39 | $CH_3(CH_2)_4$ | $CH_2-CH(CH_3)_2$ | 95 | 2.6 |
| 40 | $CH_3$ | cyclopropyl with $-CH_2CH_3$ and $CH_3$ | 100 | 0.45 |
| 41 | $(CH_3)_2CH$ | cyclopropyl with $-CH_3$ and $CH_3$ | 98 | 0.54 |
| 42 | $CH_3$ | cyclopropyl with $-CH_2CH_3$ and $CH_2CH_3$ | 98 | 0.86 |

TABLE I-continued $$R^3-\overset{*}{C}=\overset{COOH}{\underset{|}{C}}-NHCOR^2$$

| Compounds Dipeptidase Inhibitor | R³ | R² | % Inhibition at $10^{-4}$ M | $K_i$ (μM) |
|---|---|---|---|---|
| 43 | CH₃ | cyclopropyl-CH₂CH₃ | 96 | 1.6 |
| 44 | CH₃ | cyclopropyl-C(CH₃)(CH(CH₃)₂) | 95 | 3 |
| 45 | CH₃CH₂ | cyclopropyl-C(CH₃)₂ | 98 | 0.18 |
| 46 | Ph | cyclopropyl-C(CH₃)₂ | 100 | 0.62 |
| 47 | CH₃CH₂CH₂ | cyclopropyl-C(CH₃)₂ | 98 | 0.11 |
| 48 | (CH₃)₂CHCH₂ | cyclopropyl-C(CH₃)₂ | 97 | 0.23 |
| 49 | CH₃(CH₂)₃ | cyclopropyl-C(CH₃)₂ | 100 | 0.11 |
| 50 | CH₃(CH₂)₄ | cyclopropyl-C(CH₃)₂ | 100 | 0.17 |
| 51 | HOOCCH₂CH₂ | cyclopropyl-C(CH₃)₂ | 98 | 0.145 |

TABLE I-continued $$R^3-\overset{*}{C}=\underset{\underset{NHCOR^2}{|}}{\overset{\overset{COOH}{|}}{C}}$$

| Compounds Dipeptidase Inhibitor | R³ | R² | % Inhibition at 10⁻⁴ M | K_i (μM) |
|---|---|---|---|---|
| 52 | cyclohexyl-CH₂ | -C(CH₃)(CH₃)- (cyclopropyl) | 100 | 0.15 |
| 53 | PhCH₂CH₂ | -C(CH₃)(CH₃)- (cyclopropyl) | 96 | 0.33 |
| 54 | CH₃SCH₂CH₂ | -C(CH₃)(CH₃)- (cyclopropyl) | 99 | 0.12 |
| 55 | CH₃SO₂CH₂CH₂ | -C(CH₃)(CH₃)- (cyclopropyl) | 96 | 0.5 |
| 56 | CH₃(CH₂)₅ | -C(CH₃)(CH₃)- (cyclopropyl) | 98 | 0.149 |
| 57 | CH₃(CH₂)₆ | -C(CH₃)(CH₃)- (cyclopropyl) | 99 | 0.092 |
| 58 | CH₃(CH₂)₉ | -C(CH₃)(CH₃)- (cyclopropyl) | 96 | 0.14 |
| 59 | PhCH₂ | -C(CH₃)(CH₃)- (cyclopropyl) | 98 | 0.44 |
| 60 | CH₃O(CH₂)₃ | -C(CH₃)(CH₃)- (cyclopropyl) |  | 0.28 |

TABLE I-continued $$R^3-\overset{*}{C}=\overset{COOH}{\underset{|}{C}}-NHCOR^2$$

| Compounds Dipeptidase Inhibitor | $R^3$ | $R^2$ | % Inhibition at $10^{-4}$ M | $K_i$ ($\mu$M) |
|---|---|---|---|---|
| 61 | $CH_3OCH_2CH_2$ | ▷⟨$CH_3$, $CH_3$ | 98 | 0.32 |
| 62 | $(CH_3)_3CCH_2$ | ▷⟨$CH_3$, $CH_3$ |  | 0.34 |
| 63 | $(CH_3)_2CHCH_2CH_2$ | ▷⟨$CH_3$, $CH_3$ | 98 | 0.15 |
| 64 | $H_2OC(CH_2)_3$ | ▷⟨$CH_3$, $CH_3$ | 99 | 0.048 |
| 65 | tetrahydrofuran-2-yl-$CH_2$ | ▷⟨$CH_3$, $CH_3$ |  | 0.39 |
| 66 | $CH_3(CH_2)_4$ | (+)▷⟨$CH_3$, $C(CH_3)_3$ |  | .08 |

Example 2

A single animal crossover study in the chimpanzee which shows increased urinary recovery was conducted as follows: A male chimpanzee, body weight 60 kg, was given 5 mg/kg of the compound 2-(1-acetimidoyl-pyrollidin-3-yl-thio)-6-(1-hydroxyethyl)-pen-2-em-3-sodio carboxylate, IV, alone, and in a second trial in combination with 5 mg/kg 7-(L-2-amino-2-carboxyethylthio)-2-(2,2-dimethylcyclopropane-carboxamido)-2-heptenoic acid. Urinary recovery of the carbapenem was 45.2% when the carbapenem was used alone, and this recovery rate rose to 73.1% when the combination was administered.

SECTION 2. EXAMPLES ILLUSTRATING CHEMICAL PREPARATIONS

The inhibitor compounds are novel compounds claimed in a copending application. These compounds are made by condensing directly the appropriate 2-keto acid and amide:

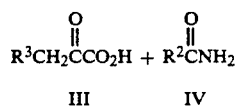

$$R^3CH_2\overset{O}{\overset{\|}{C}}CO_2H + R^2\overset{O}{\overset{\|}{C}}NH_2 \quad\quad II$$
$$\text{III} \quad\quad \text{IV}$$

wherein $R^2$ and $R^3$ are as defined. The general reaction conditions involve mixing approximately 1–4:1 parts of the acid to the amide in an inert solvent such as toluene or methyl isovalerate and heating at reflux with azeotropic removal of water for from 3–48 hours, preferably 5–24 hours. The solution when cooled normally yields the product in crystalline form, but the product can also be isolated using a base extraction process. The product can be recrystallized by using generally known techniques. An optional modification of this procedure requires an additional small amount of p-toluenesulfonic acid as catalyst during the reaction.

Another route to the novel inhibitor compounds uses an α-amino acid, t-butyl ester in reaction with an acid chloride:

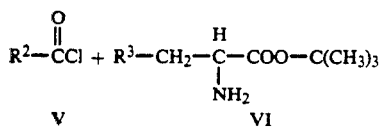

This reaction takes place in the presence of base, such as triethylamine, in a solvent such as methylene chloride. The resulting N-acylated product (VII) is then oxidized by treatment with t-butyl hypochlorite followed by addition of sodium methoxide. This yields the 2-methoxy derivative (VIII) and/or its elimination product, the α,β-unsaturated ester (IX). Further treatment with anhydrous hydrochloric acid converts either VIII or IX (or the mixture of both) to the desired α,β-unsaturated free acid (II).

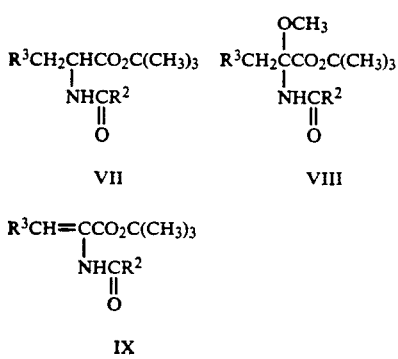

Some compounds wherein $R^3$ has a terminal substituent which is an amino, quaternary nitrogen, thiol or carboxyl, derivative can be made most conveniently from an intermediate having a terminal bromine. In this case the intermediate has the structure

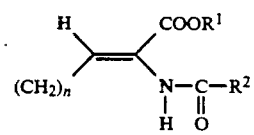

wherein n is the number of carbons in the desired hydrocarbon chain (e.g., from 3-7). In order to prepare $R^3$ having a terminal trimethylammonium substituent, the bromo intermedaite is reacted with trimethylamine; to yield the amino, the bromo intermediate is reacted with ammonia; the guanidino, reaction is with guanidine; to prepare the thio derivatives, including 2-amino-2-carboxxethylthio, the bromo compound is reacted with cysteine HCl, or the appropriate mercaptan. Derivatized amino, such as formamidino, ureido, and acylamide (acetamido) can be made from the compounds having an amino group by reacting with o-benzyl formimidate HCl, potassium cyanate and the appropriate acyl anhydride (acetic anhydride), respectively.

Another route for preparing compounds when $R^3$ is a terminally substituted thio derivative utilizes a chloroketo ester intermediate:

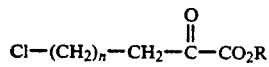

in reaction with the desired amide,

in toluene at reflux in the presence of a catalytic amount of p-toluenesulfonic acid. The resulting intermediate is hydrolyzed to the acid; the chloro group is then displaced in reaction with the appropriate mercaptan. This reaction is valuable since it permits use of the chiral amide IV, thereby preparing a functionalized side chain. In addition, the mixture of Z+E isomers prepared after the mercaptan condensation can be directly isomerized into the Z form by adding acid to a pH about 3, and heating to about 90° C. for 30 minutes. Only the Z form remains, and recovery is simple and straight forward.

More detail about preparation of the compounds is found in the following examples.

Example 3

Z-2-Isovaleramido-2-butenoic Acid

A solution of 1.07 g (10.5 mmole) of 2-keto-butyric acid and 0.71 g (7.0 mmole) of isovaleramide in 15 ml of toluene was stirred under reflux with collection of $H_2O$ in a small Dean-Stark trap. After 5 hrs, the solution was cooled, resulting in fairly heavy crystallization. After standing, the solid was collected on a filter and washed with toluene and then with $CH_2Cl_2$. Yield of white crystals=0.47 g, mp 172°-174° (slight prelim. softening). The material was recrystallized from diisopropyl ketone. Tlc (4:1 toluene-AcOH) now showed only a faint trace of the other isomer. Yield of white crystals=0.32 g (25%), mp 175° (slight prelim. softening). NMR indicated essentially exclusively Z-isomer.

| | Anal. ($C_9H_{15}NO_3$) | |
|---|---|---|
| | Calcd. | Found |
| C | 58.36 | 58.59 |
| H | 8.16 | 8.55 |
| N | 7.56 | 7.43 |

Example 4

Z-2-(2,2-Dimethylcyclopropanecarboxamido)-2-pentenoic acid

A solution of 1.74 g (15 mmole) of 2-ketovaleric acid and 1.13 g (10 mmole) of 2,2-dimethylcyclopropanecarboxamide in 20 ml of toluene was refluxed with stirring with collection of $H_2O$ in a small Dean-Stark trap. After 20 hrs. the solution was cooled and treated with a gentle stream of $N_2$. Before much of the solvent had evaporated, crystallization was induced by scratching. After standing, the solid was collected on a filter and washed with toluene and some $Et_2O$. Yield of white crystals=0.63 g (30%), mp 154.5°-155.5° (slight prelim. softening). Tlc (4:1 toluene-AcOH) showed only an extremely faint trace of the other isomer. NMR was consistent with the Z-configuration.

| | Anal. ($C_{11}H_{17}NO_3$) | |
|---|---|---|
| | Calcd. | Found |
| C | 62.53 | 62.86 |
| H | 8.11 | 8.27 |

-continued

| Anal. (C₁₁H₁₇NO₃) | |
|---|---|
| Calcd. | Found |
| N 6.63 | 6.75 |

EXAMPLE 5

Z-2-2-(3-Cyclopentylpropionamido)-2-butenoic acid

A solution of 1.41 g (10 mmole) of 3-cyclopentylpropionamide and 1.53 g (15 mmole) of 2-ketobutyric acid was stirred and refluxed under a small Dean-Stark trap. After 8 hrs. the solution was cooled, resulting in heavy crystallization. The solid was collected on a filter and washed with toluene and $CH_2Cl_2$. Yield of white crystals=1.44 g, mp 180.5°-182° (prelim. softening). The material was recrystallized from methyl ethyl ketone. Yield of white needles=0.63 g (28%), mp 184°-185° (slight prelim. softening). Tlc (4:1 toluene-AcOH) now showed a single spot, and NMR indicated essentially pure Z-isomer.

| Anal. ($C_{12}H_{19}NO_3$) | |
|---|---|
| | Calcd. | Found |
| C | 63.97 | 63.99 |
| H | 8.50 | 8.67 |
| N | 6.22 | 6.27 |

EXAMPLE 6

Z-2-(2-Ethylhexanamido)-2-butenoic acid 10 g. of 2-ethylhexanoyl chloride was added dropwise with stirring to 25 ml of cold conc. $NH_4OH$ solution, resulting in immediate precipitation. The mixture was allowed to stir for 2 hrs., then filtered, and air dried to give 6.5 g. of amide. 1.4 g (10 mmole) of the above compound and 1.5 g of ketobutyric acid (15 mmole) were refluxed in 25 ml toluene for 15 hrs with removal of water. The reaction mixture was cooled and partly evaporated with a stream of $N_2$. Crystallization of product occurred after standing for 3 hrs. The crystals were collected, washed 3×with toluene, and air dried. There was isolated 1.13 g (50%) of product, mp 160°-162°. NMR was in accord with the assigned structure and indicated <5% E isomer. Tlc (4:1 toluene-AcOH) showed a single spot.

| Anal. ($C_{12}H_{21}NO_3$) | |
|---|---|
| | Calcd. | Found |
| C | 63.40 | 63.63 |
| H | 9.30 | 9.43 |
| N | 6.16 | 5.88 |

EXAMPLE 7

Z-2-(2,2-Dimethylcyclopropanecarboxamido)-2-butenoic acid 1.53 g (15 mmoles) of 2-ketobutyric acid, 1.13 g (10 mmoles) of 2,2-dimethylcyclopropanecarboxamide and 20 ml of toluene stirred at reflux for 10 hours. After cooling the crystalline solid was filtered and washed with toluene (3×10 ml) and dried to give 1.06 g of product, mp 140°-141° C. Tlc (4:1 toluene-AcOH) showed essentially one spot and the NMR spectrum fit the desired structure.

Recrystallization from EtOAc gave after drying 0.533 g of product mp 142°-143.5°, homogeneous by tlc.

| Anal. ($C_{10}H_{15}NO_3$) | |
|---|---|
| | Calcd. | Found |
| C | 60.90 | 60.92 |
| H | 7.67 | 7.71 |
| N | 7.10 | 7.38 |

EXAMPLE 8

Z-2-(2,2-Dimethylcyclopropanecarboxamido)-2-hexenedioic acid

A mixture of 1.0 g. of 2,2-dimethylcyclopropanecarboxamide, 2.4 g. of 2-ketoadipic acid and 25 ml. of methyl isovalerate was heated under reflux for 4 hrs, with removal of $H_2O$ by a modified Dean-Stark trap containing molecular sieves (4A). After standing at room temperature overnight, the crystalline precipitate was filtered, washed with ether and recrystallized from ethyl acetate to give 0.23 g. of product, m.p. 163°-165°. The NMR spectrum was consistent with the desired structure.

| Anal. ($C_{12}H_{17}NO_5$) | |
|---|---|
| | Calcd. | Found |
| C | 56.46 | 56.20 |
| H | 6.71 | 6.83 |
| N | 5.49 | 5.32 |

Example 9

Z-2-(2,2-Diethylcyclopropanecarboxamido)-2-butenoic acid

A mixture of 2.3 g of 2-ketobutyric acid, 2.0 g of 2,2-diethylcyclopropanecarboxamide, and 25 ml of toluene was heated under reflux for 16 hrs with removal of $H_2O$ by a modified Dean-Stark trap containing molecular sieves (4A). No product precipitated upon cooling. Ether (25 ml) was added and the mixture was extracted with saturated $NaHCO_3$ (3 times). The combined extracts were acidified with concentrated HCl. The gummy precipitate crystallized when triturated with water. Recrystallization from ethyl acetate gave 0.31 g of product, m.p. 129°-30°. The NMR spectrum was consistent with the desired structure.

| Anal. ($C_{12}H_{19}NO_3$) | |
|---|---|
| | Calcd. | Found |
| C | 63.98 | 64.01 |
| H | 8.50 | 8.62 |
| N | 6.22 | 6.21 |

Example 10

2-(2,2-Dimethylcyclopropanecarboxamido)-2-hexenoic acid

Step A: DL-Norleucine t-butyl ester

General procedure of R. Roeske, *J. Org. Chem.* 28, p. 1251 (1963).

To a suspension of 9.82 g (75 mmole) of DL-norleucine in 80 ml of dioxane in a 500 ml. pressure bottle cooled in an ice bath was added slowly (with swirling)

8 ml of concentrated H$_2$SO$_4$. The resulting mixture was cooled in a dry ice bath as 80 ml of liquid isobutylene was added. The mixture was allowed to warm to room temperature and shaken under autogenous pressure for ~23 hrs. After most of the isobutylene had been vented off, the slightly hazy solution was cooled in ice and then added to a cold mixture of 400 ml of 1N NaOH and 500 ml of Et$_2$O. After shaking in a separate funnel, the layers were separated, and the aqueous fraction was washed with an additional 100 ml of Et$_2$). The Et$_2$O solution was shaken with 150 ml of 0.5N HCl. The acidic aqueous fraction was treated with 2.5N NaOH until strongly basic and then shaken with 250 ml of Et$_2$O. The Et$_2$O solution was dried (MgSO$_4$), filtered, and concentrated on the rotovac. After prolonged pumping on high vacuum over a steam bath, final yield of clear, colorless residual oil=9.04 g (65%). NMR now showed only a trace of dioxane. TLC (9:1 CHCl$_3$—MeOH) showed a single spot.

Step B: N-(2,2-Dimethylcyclopropanecarbonyl)-DL-norleucine t-butyl ester

To a solution of 8.98 g (48 mmole) of DL-norleucine t-butyl ester and 5.05 g (50 mmole) of triethylamine in 100 ml of CH$_2$Cl$_2$ stirred in an ice bath under a drying tube was added dropwise (over a period of 75 min.) a solution of 6.39 g (48 mmole) of 2,2-dimethylcyclopropanecarbonyl chloride (M. Elliot and N. R. James, British Patent No. 1,260,847 (1972)) in 50 ml of CH$_2$Cl$_2$. Precipitation of Et$_3$N HCl occurred during the addition, especially toward the end. As the ice gradually melted, the mixture was allowed to warm to room temperature. After 16 hrs, the mixture was shaken with 200 ml of 0.5N HCl. The CH$_2$Cl$_2$ fraction was washed with an additional 200 ml of 0.5N HCl, then with 2×200 ml of 0.5N NaOH, and finally 200 ml of H$_2$O. The CH$_2$Cl$_2$ fraction was dried with MgSO$_4$, treated with charcoal, and filtered through Celite. The filtrate was concentrated on the rotovac (finally under high vacuum). Yield of light orange residual oil=11.93 g (88%). Tlc (2:1 hexane-EtOAc) showed a single spot. NMR and IR were in accord with the assigned structure. After standing for several days, the unused portion of this material crystallized: m.p. 52°→65°.

Step C: t-Butyl 2-(2,2-dimethylcyclopropanecarboxamido)-2-methoxyhexanoate

Based on procedure of H. Poisel and V. Schmidt, *Chem. Ber.*, 108 p. 2547 (1975).

To a solution of 6.37 g (22.5 mmole) of N-(2,2-dimethylcyclopropanecarbonyl)-DL-norleucine t-butyl ester in 35 ml of Et$_2$O stirred at room temperature under N$_2$ in the dark was added 2.69 ml (2.45 g, 22.5 mmole) of t-butyl hypochlorite. After 15 min., a solution of sodium methoxide prepared by dissolving 0.52 g (22.6 mmole) of sodium in 35 ml of MeOH was added. Stirring was continued at ambient temperature under N$_2$ in the dark. After 16.5 hrs., the precipitated NaCl was filtered off. The filtrate was diluted with Et$_2$O and washed successively with 3×50 ml of 0.5N HCl, 50 ml of saturated Na$_2$CO$_3$, and 2×50 ml of H$_2$O. The Et$_2$O phase was dried over MgSO$_4$ and filtered. The filtrate was concentrated on the rotovac. The pale, golden-yellow residual oil (6.45 g) was subjected to preparative high pressure liquid chromatography, resulting in the separation and isolation of 273 mg and 496 mg of the two diastereomers of t-butyl 2-(2,2-dimethylcyclopropanecarboxamido)-2-methoxyhexanoate (respective mp's 114°-118° and 124°-125.5°) as well as 1.97 g of a single isomer (apparently Z) of t-butyl 2-(2,2-dimethylcyclopropanecarboxamido)-2-hexenoate (colorless oil).

Step D: 2-(2,2-Dimethylcyclopropanecarboxamido)-2-hexenoic acid

A solution of 0.84 g (3.0 mmole) of t-butyl 2-(2,2-dimethylcyclopropanecarboxamido)-2-hexenoate in 10 ml of Et$_2$O saturated with anhydrous HCL was allowed to stand at room temperature under a drying tube. After 17 hrs, the solution was evaporated, and the residual gum was dissolved in 10 ml of saturated NaHCO$_3$. This solution was washed with an additional 15 ml of 0.5N HCl, then dried (MgSO$_4$), filtered, and concentrated to give a viscous oil. The oil was crystallized from toluene. Yield of white crystals=0.32 g (47%), m.p. 119°-122°. TLC (4:1 toluene-AcOH) showed a single spot. NMR indicated essentially pure Z-isomer. (Note: Treatment of the methanol adduct, t-butyl 2-(2,2-dimethylcyclopropanecarboxamido)-2-methoxyhexenoate, with anhydrous HCl in Et$_2$O under similar conditions gave the same product.)

Example 11

(+)-Z-2-(2,2-Dimethylcyclopropanecarbonylamino)-2-octenoic acid, sodium salt

The reagents, (+)-2,2-dimethylcyclopropanecarboxamide, 7.0 g.; 2-keto-octanoic acid ethyl ester, 14.7 g.; 50 mg. of p-toluene sulfonic acid; and 100 ml. of toluene was changed to a 250 ml. three-necked flask under a Dean Stark trap containing several molecular sieve pellets. The mixture was refluxed vigorously for 27 hours. The resultant light yellow solution was cooled and concentrated in vacuo, at a water bath temperature of 45° C., in the presence of water to help remove toluene. The gummy residue was suspended in 230 ml. of 2N NaOH and stirred at 30° C. for 3 hours; then the temperature was raised to 35° C. for an additional 2½ hrs. until a clear solution formed. The solution was then cooled, 85 ml. methylene chloride added, and the pH adjusted to 8.5 using 4N HCl with stirring. The organic layer was separated and discarded. The aqueous layer (366 ml.) was assayed by liquid chromatography to contain 37.2 mg/ml; 87% Z isomer. Another 85 ml. portion of CH$_2$Cl$_2$ was then added and pH adjusted to 4.5 with stirring. The organic layer was separated and the aqueous layer reextracted with 50 ml. of CH$_2$Cl$_2$, with the pH again adjusted to 4.5. Combined organic extracts were dried over Na$_2$SO$_4$, filtered, and concentrated to a gum. This residue was dissolved in 150 ml. isopropanol and 15 ml. water and the pH adjusted to 8.2 with 2N NaOH. The resulting solution was concentrated to an oily residue which was flushed with isopropanol until it turned to a crystalline solid, indicating that most water had been removed. It was crystallized from 120 ml. of isopropanol, (cooled in ice for 1 hour) filtered, and washed with 50 ml. cold isopropanol followed by copious amounts of acetone. It was dried at 60° C./0.1 mm/2 hours to yield 10.74 g (63.2%) crystalline material, having essentially a single peak in liquid chromatography, m.p. 241°-243° C.

The starting material, (+)-2,2-dimethylcyclopropanecarboxamide is most conveniently prepared by resolution of the D,L acid, followed by reaction with oxalyl chloride and then ammonia to give the resolved amide.

One way of making the starting material is as follows: 23.1 g. of D,L-2,2-dimethylcyclopropanecarboxylic acid was suspended in 33 ml H$_2$O and the pH adjusted to 8.0, using 50% NaOH, about 10 ml. To this was added a solution of 38.4 g quinine in a mixture of 60 ml. methanol and 30 ml. H₂O to which had been added about 8 ml of concentrated HCl in another 30 ml. H₂O to give a pH of 7.1. (This was actually a solution of quinine hydrochloride.)

These solutions were added all at once, with stirring. The gummy crystalline material which formed was heated to give two clear layers and again stirred vigorously while cooling to give a crystalline product. This product was permitted to stand over two days at room temperature. It was then filtered, washed with 2×10 ml water, and 2×10 ml 50% methanol, and air dried with suction. The yield of crude quinine salt was 44.8 g (48.7% yield) monohydrate, m.p. 113°-116° C., having a $[\alpha]_D^{20}$ of −94.3°, C=1.0; CHCl₃. This material was recrystallized from acetone to yield 24.35 g, m.p. 127°-130° C. This purified quinine salt was converted to the acid by reaction with aqueous base and chloroform, followed by acid, to yield (96%) 3.9 g having $[\alpha]_D^{20}$ of +146.0°.

This acid was converted to the amide as follows: A charge of 30.5 g (+)acid was added over 5-10 minutes through a dropping funnel to chilled (10° C.) oxalyl chloride, 54 ml., containing 1 drop dimethylformamide. This was stirred overnight at ambient temperature. A clear solution was observed, which was added to 100 ml. methylene chloride to dilute. Excess oxalyl chloride was removed by concentrating and the mixture flushed twice with methylene chloride.

The resultant solution was diluted with an equal volume of methylene chloride, and added continuously through a dropping funnel to about 100 ml. anhydrous liquid ammonia which was diluted with 100 ml methylene chloride. A dry ice-acetone cooling bath was used during the addition. When all was added, the cooling bath was removed and the mixture stirred at room temperature for about ½ hour. The mixture was filtered, to remove precipitated ammonium chloride, and concentrated to dryness. The crude weight was 26.6 g. (88%). It was redissolved in excess hot ethyl acetate and filtered through a preheated sintered glass funnel to separate from trace NH₄Cl. Excess ethyl acetate was atmospherically distilled off. When half the volume remained, 130 ml of heptane were added, and ethyl acetate was continued to be distilled off, until the boiling point started to rise (to near 80° C.; much of product had already crystallized out). Heat was removed, and the mixture let cool gradually to about 30° C., then cooled with an ice bath to 0°-5° C. for about ½ hour. The product was recovered as nice silverywhite crystalline flakes, washed with 3× ethyl acetate/hexane mixture, 1/1.5 and air dried to constant weight. It weighed 23.3 g (77.1% yield overall, 87.6% recovery from crude), m.p. =135°-138° C. (varies with rate of heating). Angle of rotation was determined by dissolving 0.0543 g in 10 ml chloroform, $[\alpha]_D^{20}$=+100.9°.

EXAMPLE 12

Z-2-(2,2-Dichlorocyclopropanecarboxamido)-2-butenoic acid

Step A: 2,2-Dichlorocyclopropanecarboxamide

A 7.1 g sample of 2,2-dichlorocyclopropanecarbonyl chloride (U.S. Pat. No. 3,301,896, issued Jan. 31, 1967) was added dropwise to 75 ml of concentrated ammonium hydroxide with vigorous stirring. The temperature of the reaction mixture was maintained below 10° C. with an ice bath. The mixture was stirred in the ice bath for 30 min., then at room temperature for 1 hr. The aqueous ammonia was evaporated under reduced pressure (bath at 50° C.). The solid residue was extracted with hot ethyl acetate (3×30 ml). The extracts were boiled down to 40 ml and 20 ml of hexane was added. After cooling in ice, the solid was filtered, washed with ethyl acetate-hexane (1:1) and dried to give 2.7 g of 2,2-dichlorocyclopropanecarboxamide, m.p. 144°-146°. The NMR spectrum was in accord with the desired structure.

| | Anal. (C₄H₅Cl₂NO) | |
|---|---|---|
| | Calcd. | Found |
| C | 31.20 | 31.26 |
| H | 3.27 | 3.31 |
| N | 9.10 | 9.11 |
| Cl | 46.04 | 45.79 |

Another 1.3 g of amide, m.p. 143°-145° could be recovered from the mother liquor.

Step B: Z-2-(2,2-Dichlorocyclopropanecarboxamido)-2-butenoic acid

A mixture of 1.53 g (15 mmoles) of 2-ketobutyric acid, 1.54 g (10 mmoles) of 2,2-dichlorocyclopropanecarboxamide and 10 ml of toluene was heated under reflux for 12 hrs. with removal of H₂O by a modified Dean-Stark trap containing molecular sieves (4A). An additional 0.7 g of 2-ketobutyric acid was added and the reaction mixture was heated under reflux for an additional 12 hrs. The mixture was cooled, diluted with 20 ml of toluene and extracted with saturated sodium bicarbonate (3×10 ml). The extracts were combined, washed with ether and acidified to pH 3 (pH meter) with concentrated hydrochloric acid. A gum precipitated which soon solidified. It was filtered, washed with water, dried and recrystallized from nitromethane to give 423 mg of Z-2-(2,2-dichlorocyclopropanecarboxamido)-2-butenoic acid, m.p. 188°-189.5° C. The NMR spectrum was in accord with the desired structure.

| | Anal. (C₈H₉Cl₂NO₃) | |
|---|---|---|
| | Calcd. | Found |
| C | 40.36 | 40.48 |
| H | 3.81 | 3.80 |
| N | 5.88 | 5.91 |
| Cl | 29.78 | 29.53 |

EXAMPLE 13

Z-2-(2,2-Dichlorocyclopropanecarboxamido)-2-octenoic acid

A mixture of 1.19 g (7.5 mmoles) of 2-ketooctanoic acid, 0.77 g (5.0 mmoles) of 2,2-dichlorocyclopropanecarboxamide, and 5 ml toluene were reacted using the same procedure as in the previous example. The crude product (537 mg) was purified by conversion to the methyl ester (BF₃/CH₃OH), prepartive TLC (silica gel G, 4:1 hexane-EtOAc) and saponification of the pure Z-methyl ester (0.3M LiOH/CH₃OH) to give 88 mg of Z-2-(2,2-dichlorocyclopropanecarboxamido)-2-octenoic acid as a partially crystalline gum. NMR spectrum (DMSO-d₆): 9.68δ (s, 1H, NH), 6.50δ (t, 1H, ), 2.83δ (t, 1H,

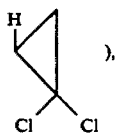
), 1.97δ (d,

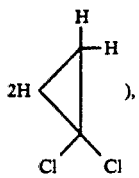
), 0.87δ (t, 3H, CH$_3$).

EXAMPLE 14

Z-8-Bromo-2-(2,2-Dimethylcyclopropanecarboxamido)-2-octenoic acid

To a suspension of 14.4 g (0.3 mole) of 50% NaH dispersion in 360 ml of toluene cooled in an ice bath and in a N$_2$ atmosphere was added over 45 min. a solution of 146 g (0.6 moles) of 1,6-dibromohexane and 57.6 g (0.3 mole) of ethyl 1,3-dithiane-2-carboxylate in 120 ml of DMF. The cooling bath was removed and the mixture stirred at room temperature for 20 hrs. The reaction mixture was washed with water (3×210 ml), dried over MgSO$_4$ and evaporated under reduced pressure to give 179.5 g of a yellow oil containing the desired alkylated dithiane, 1,6-dibromohexane and mineral oil. This crude material was used in the next reaction without purification.

To a suspension of 426 g (2.4 moles) of N-bromosuccinamide in 800 ml of acetonitrile and 200 ml of H$_2$O was added over 45 min. a solution of the crude dithiane in 100 ml of acetonitrile. The temperature of the reaction mixture was maintained below 25° C. with an ice bath. After stirring at 20° C. for 10 min. the dark red reaction mixture was poured into 2 l. of hexane-CH$_2$Cl$_2$ (1:1). The solution was shaken with saturated NaHSO$_3$ (2×400 ml) and water (1×500 ml). Then 400 ml of saturated Na$_2$CO$_3$ solution was added in small portions (vigorous CO$_2$ solution). After the foaming subsided the funnel was shaken and the aqueous phase separated. The organic layer was extracted with saturated Na$_2$CO$_3$ solution (400 ml) and water (500 ml) and dried over MgSO$_4$. Removal of the solvent under reduced pressure gave 133.8 g of crude bromo ketoester containing 1,6-dibromohexane and mineral oil. This crude material was used in the next reaction without purification.

A mixture of 133.8 g of crude bromo ketoester, 133 ml of 50% hydrobromic acid and 267 ml of acetic acid was heated at 90° C. (internal temperature) for 75 min. The dark solution was evaporated under reduced pressure until most of the acetic acid was removed. The residue was dissolved in 500 ml of ether, washed with water (2×100 ml) and extracted with saturated NaHCO$_3$ (3×200 ml). The combined NaHCO$_3$ extracts were extracted with ether (2×100 ml) and acidified with concentrated HCl. The precipitated oil was extracted with ether (3×200 ml). The ether extracts were washed with water (1×100 ml) and saturated brine (1×100 ml) and dried over MgSO$_4$. Removal of the ether under reduced pressure gave 46.2 g of pure bromoketo acid. Homogeneous by TlC (silica gel, 4:1 toluene-acetic acid). The NMR spectrum was consistent with the desired product.

A mixture of 46.1 g (0.194 moles) of the bromoketo acid, 17.6 g (0.156 mole) of 2,2-dimethylcyclopropanecarboxamide and 450 ml of toluene was heated under reflux for 13 hrs., with collection of water in a small Dean-Stark trap. After cooling, the clear reaction mixture was extracted with saturated NaHCO$_3$ solution (4×100 ml). The combined extracts were washed with ether (2×100 ml) and then the pH was adjusted to 3.5 (pH meter) by addition of concentrated HCl. An oil precipitated which soon crystallized. The solid was filtered, washed well with water and dried. Recrystallization from acetonitrile gave 22.5 g of Z-8-bromo-2-(2,2-dimethylcyclopropanecarboxamido)-2-octenoic acid, m.p. 151°–153° C. Homogeneous by TLC (4:1 tolueneacetic acid). The NMR spectrum was consistent with the desired structure.

| Anal. (C$_{14}$H$_{22}$BrNO$_3$) | | |
|---|---|---|
| | Calcd. | Found |
| C | 50.61 | 50.66 |
| H | 6.67 | 6.96 |
| N | 4.22 | 4.45 |
| Br | 24.05 | 23.95 |

The following ω-bromo compounds were prepared using the same procedure:

Z-6-Bromo-2-(2,2-dimethylcyclopropanecarboxamido)-2-hexenoic acid;

Z-7-Bromo-2-(2,2-dimethylcyclopropanecarboxamido)-2-heptenoic acid;

Z-9-Bromo-2-(2,2-dimethylcyclopropanecarboxamido)-2-2-nonenoic acid;

Z-10-Bromo-2-(2,2-dimethylcyclopropanecarboxamido)-2-decenoic acid;

Z-8-Bromo-2-(2,2-dichlorocyclopropanecarboxamido)-2-octenoic acid.

EXAMPLE 15

Z-8-Dimethylamino-2-(2,2-dimethylcyclopropanecarboxamido)-2-octenoic acid

A solution of 664 mg (2 mmoles) of Z-8-bromo-2-(2,2-dimethylcyclopropanecarboxamido)-2-octenoic acid in 10 ml of 40% aqueous dimethylamine was allowed to stand at room temperature for 4 hrs. The solution was poured onto a 3.5×20 cm column of Dowex 50W-x8 (100–200 mesh, H+) ion exchange resin and the column eluted with water until the effluent was no longer acidic (~200 ml). The column was then eluted with 300 ml of 2N ammonium hydroxide. The effluent was evaporated under reduced pressure to give 600 mg of a colorless glass. This material was dissolved in 3 ml of ethanol, filtered, and added dropwise to 200 ml of rapidly stirred acetone. A gummy solid precipitated which crystallized upon stirring for two days. The solid was filtered, washed with acetone, and dried to give 445 mg of Z-8-dimethylamino-2-(2,2-dimethylcyclopropanecarboxamido)-2-octenoic acid as colorless, hygroscopic crystals, m.p. 101°–112° C. Homogeneous by TLC (silica gel, in BuOH, HOAc, H$_2$O, 4:1:1). NMR spectrum was consistent with desired structure.

| Anal. ($C_{16}H_{28}N_2O_3 \cdot H_2O$) | | |
|---|---|---|
| | Calcd. | Found |
| C | 61.12 | 61.03 |
| H | 9.62 | 9.28 |
| N | 8.91 | 8.67 |

The following ω-amino derivatives were prepared using essentially the same procedure.

Z-10-Dimethylamino-2-(2,2-dimethylcyclopropanecarboxamido)-2-decenoic acid;
Z-8-Amino-2-(2,2-dimethylcyclopropanecarboxamido)-2-octenoic acid;
Z-8-Dimethylamino-2-(2,2-dimethylcyclopropanecarboxamido)-2-octenoic acid;
Z-7-Dimethylamino-2-(2,2-dimethylcyclopropanecarboxamido)-2-heptenoic acid;
Z-2-(2,2-dimethylcyclopropanecarboxamido)-7-(N-methylpiperazinyl)-2-heptenoic acid;
Z-2-(2,2-dimethylcyclopropanecarboxamido)-8-pyrrolidino-2-octenoic acid;
Z-2-(2,2-dimethylcyclopropanecarboxamido)-8-(N-methylpiperazinyl)-2-octenoic acid;
Z-8-Allylamino-2-(2,2-dimethylcyclopropanecarboxamido)-2-octenoic acid;
Z-2-(2,2-dimethylcyclopropanecarboxamido)-8-piperidino-2-octenoic acid;
Z-2-(2,2-dimethylcyclopropanecarboxamido)-8-propargylamino-2-octenoic acid;
Z-8-N-[1-Deoxy-(1-methylamino)-D-glucityl]-2-(2,2-dimethylcyclopropanecarboxamido)-2-octenoic acid;
Z-8-(1-Adamantylamino)-2-(2,2-dimethylcyclopropanecarboxamido-2-octenoic acid;
Z-8-Diallylamino-2-(2,2-dimethylcyclopropanecarboxamido-2-octenoic acid;
Z-8-(2,2-dimethylcyclopropanecarboxamido)-8-(2-hydroxyethylmethylamino)-2-octenoic acid;
Z-8-[(Carboxylmethyl)methylamino]-2-(2,2-dimethylcyclopropanecarboxamido)-2-octenoic acid;
Z-2-(2,2-dimethylcyclopropanecarboxamido)-8-diethylamino-2-octenoic acid;
Z-2-(2,2-dimethylcyclopropanecarboxamido)-8-[tris(hydroxymethyl)methylamino]-2-octenoic acid;
Z-2-(2,2-dimethylcyclopropanecarboxamido)-10-(N-methylpiperazinyl)-2-decenoic acid;
Z-2-(2,2-dimethylcyclopropanecarboxamido)-8-[1-(phosphono)ethylamino]-2-octenoic acid;

Example 15A

Z-8-[(Carboxymethyl)methylamino]-2-2,2-dimethylcyclopropane carboxamido)-2-octenoic acid 3.32 g of Z-8-bromo-2-(2,2-dimethylcyclopropane carboxamido)-2-octenoic acid, 1.0 g of $CH_3NH\ CH_2—CO_2H$, 3.5 g of $Na_2CO_3$ and 30 ml of water were heated at 80° C. in $N_2$ for 1.5 hours. After purification, 1.0 g of product was prepared, calc. for $C_{17}H_{28}N_2O_5 \cdot 2H_2O$: C, 54.24; H, 8.57; N, 7.44; found C, 54.40; H, 8.34; N, 7.16.

Example 15B

Z-2-(2,2-dimethylcyclopropanecarboxamido)-8-[1-(phosphono)ethylamino]-2-octenoic acid was prepared reacting the same bromo intermediate (335.1 mg) with 138.2 mg 1-aminoethane phosphoric acid, 435 mg $Na_2CO_3$ in 5 ml water, following essentially the same procedure, Ki=0.16.

Example 16

Z-2-(2,2-Dimethylcyclopropanecarboxamido)-8-methylthio-2-octenoic acid

A stream of $CH_3SH$ gas was bubbled through a solution of 162 mg (3 mmoles) of sodium methoxide in 5 ml of methanol for 10 min. with cooling in an ice bath. The solution was allowed to warm to room temperature and 332 mg (1 mmole) of Z-8-bromo-2-(2,2-dimethylcyclopropanecarboxamido)-2-octenoic acid was added. The solution was heated under reflux for 30 min. in a $N_2$ atmosphere. Most of the methanol was evaporated under reduced pressure, the residue 2.5N HCl. The precipitated oil was extracted with ether (3×). The ether extracts were washed with water, saturated brine and dried over $MgSO_4$. Removal of the ether under reduced pressure gave a colorless oil that crystallized upon standing. It was recrystallized from ether-hexane to give 178 mg of Z-2-(2,2-dimethylcyclopropanecarboxamido)-8-methylthio-2-octenoic acid, m.p. 82°–84° C. Homogeneous by TLC (toluene-acetic acid, 4:1). The NMR spectrum was in accord with the desired structure.

| Anal. ($C_{15}H_{25}NO_3S$) | | |
|---|---|---|
| | Calcd. | Found |
| C | 60.18 | 60.36 |
| H | 8.42 | 8.68 |
| N | 4.68 | 4.59 |
| S | 10.69 | 10.87 |

The following compounds were prepared by similar methods.

Z-2-(2,2-dimethylcyclopropanecarboxamido)-8-ethoxythiocarbonylthio-2-octenoic acid;
Z-2-(2,2-dimethylcyclopropanecarboxamido)-8-(1-methyl-5-tetrazolylthio)-2-octenoic acid;
Z-2-(2,2-dimethylcyclopropanecarboxamido)-7-{[(methoxycarbonyl)methyl]thio}-2-heptenoic acid;
Z-8-Acetylthio-2-(2,2-dimethylcyclopropanecarboxamido)-2-octenoic acid;
Z-7-[(2-Amino-2-oxoethyl)thio]-2-(2,2-dimethylcyclopropanecarboxamido)-2-heptenoic acid;
6-(L-2-Amino-2-carboxyethylthio)-2-(2,2-dimethylcyclopropanecarboxamido)-2-hexenoic acid;
Z-8-(Carbomethoxymethylthio)-2-(2,2-dimethylcyclopropanecarboxamido)-2-octenoic acid;
Z-6-(Carbomethoxymethylthio)-2-(2,2-dimethylcyclopropanecarboxamido)-2-hexenoic acid;
Z-2-(2,2-dimethylcyclopropanecarboxamido)-6-(phosphonomethylthio)-2-hexenoic acid.

The compound 7-(L-amino-2-carboxyethylthio)-2-(2,2-dimethylcyclopropanecarboxamido)-2-heptenoic acid is prepared in a similar fashion as the above example, except that Z-7-bromo-2-(2,2-dimethylcyclopropanecarboxamido)-2-heptenoic acid (prepared as in Example 17) (185 mg, 1.05 mmoles) is dissolved in 2.02 ml NaOH solution (2.0N), and deoxygenated by bubbling a stream of nitrogen gas through it for a minute. Then cysteine.HCl (185 mg, 1.05 mmoles) is added all at once and the reaction stirred at room temperature in a $N_2$ atmosphere for 3 hours. The reaction mixture is applied to 2×20 cm column of Dowex 50×4 (100–200 mesh, H+), and eluted with 300 ml $H_2O$, then 200 ml of 2N $NH_3$ solution. Ammonia evaporated under reduced pressure to give 284 mg of a yellowish glass. This product is dissolved in 4 ml ethanol, and the insoluble material filtered. The filtrate is added dropwise to rapidly stirred diethylether (150 ml). The solid which precipitates is filtered, washed with ether and dried to yield 171 mg product, having one : ,ot (ninhydrin positive) in TLC (μBuOH, HOAc, H₂O; ¹:1) rf.about 6; NMR is consistent with the desired structure.

| | Anal. (C₁₆H₂₆N₂O₅S) | |
|---|---|---|
| | Calcd. | Found |
| C | 53.61 | 52.55 |
| H | 7.31 | 7.40 |
| N | 7.81 | 7.89 |
| S | 8.94 | 9.63 |

Example 16A

Sodium
Z-7-(L-amino-2-Carboxyethylthio)-2-(2,2-dimethylcyclopropane carboxamido)-2-heptenoic acid A. Grignard preparation of Ethyl-7-Chloro-2-oxoheptanoate Equimolar amounts (8 moles each) of 1-bromo-5-chloropentane and magnesium are reacted in tetrahydrofuran (960 ml) at 25° C. The flask is charged with the Mg in the THF and the bromochloropentane added over 1 hour, then aged 2 hours. After the reaction was judged complete, the reaction solution was added (cooled −15° C., to 16 moles of diethyloxalate in 1856 ml tetrahydrofuran, while maintaining the temperature at 10° C. 3N HCl was added to quench, keeping the temperature below 25° C. After stripping solvents, the calculated yield is 48.8% of the ethyl-1-chloro-6-oxoheptenoate.

B. Condensation and Hydrolysis

S-2,2-dimethylcyclopropyl carboxamide (1017 g), 2143.6 g of ethyl-7-chloro-2-ketoheptanoate, 9 liters of toluene and 12 g of p-toluene sulfonic acid were charged to a 22 L flask, and heated to reflux with stirring. After 23 hours, liquid chromatography showed the expected product ratio, and 4 L of toluene were removed under slightly reduced pressure. The pot was charged with water, neutralized to pH 7 with 2N NaOH, and vacuum distilled leaving a final pot volume of about 5 liters.

This was hydrolyzed by adding 1760 g of 50% aq. NaOH (4 liters water) and stirring overnight. The flask was charged with 4 L methylene chloride, and pH adjusted to 8.8 using HCl. Unreacted amide crystallized out. The organic layers were separated from water, and then evaporated. The gummy residue was dissolved in 8 L water containing 720 g, 50% NaOH, and to this solution was charged 1818 g L-cysteine HCl.H₂O, 2 kg ice, 2484 g 50% NaOH and 1 L water.

The pH of this solution, after aging overnight at room temperature, is adjusted to 3.0 with conc. HCl, and the resulting gummy suspension heated to 95° C. to afford a clear solution. After 30 minutes, no E isomer could be detected by lc. After work-up and purification, the overall yield was 2060 g, 87% yield. This material was recrystallized from acetonitrile. 1500 g of the recrystallized material was dissolved in 6 L water and 910 ml 3.88 N NaOH, then neutralized to pH 7, and lyophilized to afford 1569 g (98.6%) of the title compound;

Analysis: Calcd., C, 50.52; H, 6.62; N, 7.36; S, 8.43; Na, 6.04; found, C. 50.71; H, 6.78; N, 7.49; S, 8.52; Na 5.92.

Example 16B

Z-8-[(2-Amino-2-oxoethyl)thio]-2-(2,2-dimethylcyclopropane carboxamido)-2-octenoic acid was also prepared in a similar manner, to that described in Example 19, above, using 3.3 gm of the bromo intermediate, 1.3 g of H₂NC(=O)CH₂SH, in 50 ml methanol. 1.6 gms of product, mp. 127°-128° C. was obtained.

Example 17

Z-2-(2,2-Dimethylcyclopropanecarboxamido)-8-trimethylammonium hydroxide-2-octenoic acid inner salt A solution of 996 mg (3 mmoles) of Z-8-bromo-2-(2,2-dimethylcyclopropanecarboxamido)-2-octenoic acid in 15 ml of 25% aqueous trimethylamine was allowed to stand at room temperature for 3 hrs. The reaction mixture was poured onto a 2×25 cm column of IRA-410 (50-100 mesh, OH⁻) ion exchange resin and eluted with water until the effluent was no longer basic. The effluent was evaporated under reduced pressure to give 800 mg of a colorless glass. This material was dissolved in 20 ml of ethanol, filtered and diluted with 600 ml of acetone. After standing at room temperature overnight the crystalline solid which deposited was filtered, washed with acetone and dried to give 720 mg of Z-2-(2,2-dimethylcyclopropanecarboxamido)-8-trimethylammonium hydroxide-2-octenoic acid inner salt as hygroscopic crystals, m.p. 220°-222° C. Homogeneous by TLC (silica gel, in BuOH, HOAc, H₂O, 4:1:1). NMR spectrum was consistent with desired structure.

| | Anal. (C₁₇H₃₀N₂O₃) | |
|---|---|---|
| | Calcd. | Found |
| C | 65.77 | 65.78 |
| H | 9.74 | 9.98 |
| N | 9.02 | 8.92 |

Other quaternary derivatives were prepared using essentially the same procedure; these are
Z-2-(2,2-Dimethylcyclopropanecarboxamido)-8-trimethylammonium hydroxide-2-octenoic acid inner salt;
Z-2-(2,2-Dimethylcyclopropanecarboxamido)-8-pyridinium hydroxide-2-octenoic acid inner salt;
Z-2-(2,2-Dimethylcyclopropanecarboxamido)-8-(2-hydroxyethyldimethylammonium hydroxide)-2-octenoic acid inner salt;
Z-2-(2,2-Dimethylcyclopropanecarboxamido)-10-trimethylammonium hydroxide-2-decenoic acid inner salt;
Z-8-(Benzyldimethylammonium hydroxide)-2-(2,2-dimethylcyclopropanecarboxamido)-2-octenoic acid inner salt;
Z-10-(Benzyldimethylammonium hydroxide)-2-(2,2-dimethylcyclopropanecarboxamido)-2-decenoic acid inner salt;
Z-2-(2,2-Dimethylcyclopropanecarboxamido)-9-trimethylammonium hydroxide-2-nonenoic acid inner salt;
Z-8-(2-Dimethylaminoethylammonium hydroxide)-2-(2,2-dimethylcyclopropanecarboxamido)-2-octenoic acid inner salt;
Z-2-(2,2-Dichlorocyclopropanecarboxamido)-8-trimethylammonium hydroxide-2-octenoic acid inner salt.

EXAMPLE 18

Z-2-(2,2-Dimethylcyclopropanecarboxamido)-8-formamidino-2-octenoic acid

A 350 mg sample of Z-8-amino-2-(2,2-dimethylcyclopropanecarboxamidoe)-2-octenoic acid was dissolved in 10 ml of water and the pH adjusted to 8.5 with 2.5N NaOH. A total of 947 mg of benzyl formimidate hydrochloride was added at room temperature in small portions over 20 min. while the pH was maintained between 8-9 by addition of 2.5N NaOH. After stirring at room temperature for 30 min., the cloudy reaction mixture was extracted with ether (3×) and applied to a 2×2.5 cm column of an AG50W-X4 (Na+, 200–400 mesh) resin. After elution with water, the fractions containing the product were pooled and evaporated under reduced pressure. This material was dissolved in water and applied to a 2×25 cm column of an AG1X8 (HCO3−, 200–400 mesh) resin. After elution with water, the fractions containing pure product were pooled and evaporated under reduced pressure. The residue was dissolved in a few ml of warm ethanol, filtered, and added dropwise to 200 ml of ether with rapid stirring. Filtration and washing with ether gave 243 mg of Z-2-(2,2-dimethylcyclopropanecarboxamido)-8-formamidino-2-octenoic acid as an amorphous solid. Homongeneous by TLC (n-BuOH, HOAc, H₂O; 4:1:1). The NMR spectrum was in accord with the desired structure.

| Anal. (C₁₅H₂₅N₃O₃·1/3H₂O) | | |
|---|---|---|
| | Calcd. | Found |
| C | 59.69 | 60.04 |
| H | 8.59 | 8.64 |
| N | 13.92 | 13.57 |

The following amidino compounds were prepared using similar procedures:

Z-8-Acetamidino-2-(2,2-dimethylcyclopropanecarboxamido)-2-octenoic acid;

Z-8-N-Benzylformamidino-2-(2,2-dimethylcyclopropanecarboxamido)-2-octenoic acid;

Z-2-(2,2-Dimethylcyclopropanecarboxamido)-10-formamidino-2-decenoic acid;

Z-2-(2,2-Dimethylcyclopropanecarboxamido)-8-(2-imidazolinyl-amino)-2-octenoic acid.

EXAMPLE 19

Z-2-(2,2-Dimethylcyclopropanecarboxamido)-8-guanidino-2-octenoic acid

To a solution of 2 mmoles of guanidine (prepared from 432 mg of guanidine sulfate and 630 mg of barium hydroxide octahydrate) in 7 ml of water was added 332 mg (1 mmole) of 8-bromo-2-(2,2-dimethylcyclopropanecarboxamido)-2-octenoic acid, and the solution was heated at 70° C. in a nitrogen atmosphere for 1 hr. The reaction mixture was applied to a 2×25 cm column of Dowex 50W-X8 (H+, 100–200 mesh). After elution with water the fractions containing the product were pooled and evaporated under reduced pressure. The residue was dissolved in several ml of warm ethanol and added dropwise to 100 ml of ether with rapid stirring. Filtration and washing with ether gave 107 mg of Z-2-(2,2-dimethylcyclopropanecarboxamido)-8-guanidino-2-octenoic acid as an amorphous electrostatic powder. Homogeneous by TLC (n-BuOH, HOAc, H₂O; 4:1:1). NMR (D₂O, NaOD): 6.48δ t, 1H,

3.10δ (m, 2H,

2.10δ (m, 2H,

1.17δ (s, 3H,

1.12δ (s, 3H,

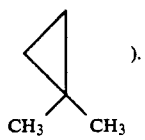

The following guanidino compound was prepared using the same procedure:

Z-2-(2,2-Dimethylcyclopropanecarboxamido)-8-(N,N-dimethylguanidino)-2-octenoic acid.

EXAMPLE 20

Z-2-(2,2-Dimethylcyclopropanecarboxamido)-8-methoxy-2-octenoic acid

To a solution of 2.43 mmoles of sodium methoxide in 5 ml of methanol was added 332 mg (1 mmole) of 8-bromo-2-(2,2-dimethylcyclopropanecarboxamido)-2-octenoic acid. The solution was heated under reflux in a nitrogen atmosphere for 1 hr. The reaction mixture was evaporated under reduced pressure, the residue dissolved in water and acidified with 2.5N hydrochloric acid. The oil which precipitated was extracted with ether (3×). The ether extracts were washed with water, and saturated brine and dried over MgSO₄. Removal of the ether under reduced pressure gave a colorless oil that crystallized upon standing. It was recrystallized from ether-hexane to give 140 mg of Z-2-(2,2-dimethylcyclopropanecarboxamido)-8-methoxy-2-octenoic acid, m.p. 71°–72° C. Homogeneous by TLC (toluene-HOAc, 4:1). The NMR spectrum was in accord with the desired structure.

| Anal. (C₁₅H₂₅NO₄) | | |
|---|---|---|
| | Calcd. | Found |
| C | 63.58 | 63.54 |
| H | 8.89 | 9.12 |
| N | 4.94 | 5.16 |

Using similar procedures, the following compounds were prepared:

Z-8-Cyano-2-(2,2-dimethylcyclopropanecarboxamido)-2-octenoic acid;
Z-7-Cyano-2-(2,2-dimethylcyclopropanecarboxamido)-2-heptenoic acid;
Z-9-Cyano-2-(2,2-dimethylcyclopropanecarboxamido)-2-nonenoic acid;
Z-2-(2,2-Dimethylcyclopropanecarboxamido)-7-sulfo-2-heptenoic acid sodium salt;
Z-2-(2,2-Dimethylcyclopropanecarboxamido)-8-sulfo-2-octenoic acid sodium salt;
Z-2-(2,2-Dimethylcyclopropanecarboxamido)-8-hydroxy-2-octenoic acid;
Z-8-Acetoxy-2-(2,2-dimethylcyclopropanecarboxamido)-2-octenoic acid.

The Z-8-cyano-2-(2,2-dimethylcyclopropanecarboxamido)-2-octenoic compound was prepared from 332 mg 8-bromo-2-(2,2-dimethylcyclopropanecarboxamido)-2-octenoic acid and 100 mg NaCN in 2 ml DMSO, heated at 80° C. for 30 minutes. After extraction and purification, 102 mg of a colorless solid, mp 99°–103° C. were recovered, analysis for $C_{15}H_{22}N_2O_3$: calcd., C, 64.73; H, 7.97; N, 10.06; found, C, 64.69; H, 8.14; N, 9.41.

The following examples illustrate preparation of representative carbapenems of formula I and intermediates thereof. Temperatures are in °celsius.

EXAMPLE 1'

STEP A:

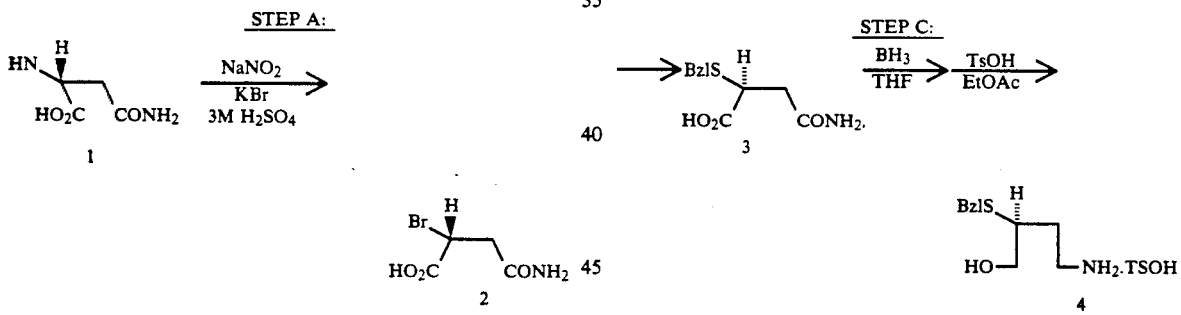

(R)-2-Bromo-3-carbamoylpropionic Acid (2)

D-Asparagine 1 (195.0 g, 1.299 mol) and KBr (461 g, 3.87 mol) were dissolved in 3M $H_2SO_4$ (1720 ml). The solution was cooled in an ice-MeOH bath and stirred while a solution of $NaNO_2$ (111.5 g. 1.62 mol) in $H_2O$ (200 ml) was added dropwise over 85 minutes. The temperature of the reaction mixture was kept at $-5°$ during the addition and for an additional 60 minutes. The white precipitate was collected, washed twice with ice-cold water, and dried i.v. to give the bromo derivative 2 (198.9 g, 78%): $[\alpha]_D + 69.0°$ (C., 4.63, EtOH).

STEP B:

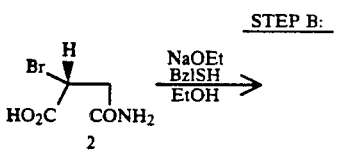

-continued
STEP B:

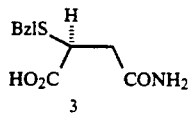

(S)-2-Benzylthio-3-Carbamoylpropionic acid (3)

A solution of sodium (50.65 g, 2.20 mol) in EtOH (2,200 ml) was cooled in an ice bath under a $N_2$ atmosphere and treated with benzyl mercaptan (293 ml, 2.50 mol). After stirring for 10 minutes at 5°–10°, the solution was treated with solid bromo acid 2 (196.00 g, 1.00 mol) in portions over 5 minutes. The resulting mixture was stirred for 2 hours at ice-bath temperature, during which time a thick, white paste formed. The mixture was dissolved in $H_2O$ (1500 ml), diluted with $Et_2O$ (1000 ml) and petroleum ether (500 ml), and shaken. The aqueous phase was separated, washed with petroleum ether (750 ml), cooled in an ice-bath, and acidified with concentrated HCl. The resulting acidic solution was stored in an ice-bath whereupon crystallization occurred. The fine, white needles were collected by filtration, washed with water, and dried i.v. to give product 3 (189.3 g, 79.1%). The mother liquors were concentrated i.v. to ca. ½ the volume and cooled in ice to give a second crop of crystals. These were collected, water washed, and dried i.v., to afford additional 3 (37.1 g, 15.5%). The two crops were combined and recrystallized from hot iPrOH (2700 ml) to give acid 3 (193.8 g) as white needles: $[\alpha]_D - 219.0°$ (c2.00, MeOH).

STEP C:

BzlS—[structure]—CONH$_2$  →  $\frac{BH_3}{THF}$  →  $\frac{TsOH}{EtOAc}$  →

BzlS—[structure]—NH$_2$·TsOH
HO
4

(S)-4-Amino-2-benzylthiol-1-butanol p-toluenesulfonic acid salt (4)

A suspension of carbamoyl acid 3 (193.0 g, 0.807 mol) in anhydrous THF (1000 ml) was stirred under a $N_2$ atmosphere at room temperature while 1M borane in THF (2150 ml, 2.15 mol) was added slowly. The resulting solution was heated at reflux for 5 hours and then kept at room temperature for 15 hours. The solution was carefully treated with 6N HCl (390 ml, 2.34 mol), then refluxed for 15 minutes and evaporated i.v. to ca. 750 ml volume. A considerable precipitate of $B(OH)_3$ was present. The mixture was cooled in an ice-bath, basified to pH 11 with 50% aqueous NaOH (180 ml), shaken with EtOAc (500 ml), and filtered. The organic phase of the filtrate was separated from the aqueous portion which was extracted with more EtOAc (2×300 ml). The combined organic solution was washed with brine, dried over anhydrous $MgSO_4$, filtered, and evaporated i.v. to a cloudy, pale yellow oil (172.25 g).

The oil was dissolved in EtOAc (100 ml) and mixed with a solution of p-toluene sulfonic acid monohydrate (155 g, 0.815 mol) in EtOAc (400 ml). The solution was cooled in an ice-bath and seeded. After ca. 1 hour, the thick, white slurry that formed was filtered and the cake was washed with cold EtOAc and Et₂O and dried i.v. to provide the salt 4 (29.5 g, 12.7%) as a white powder. The mother liquors were stored at −20° to give additional crystals of 4 (16.0 g, 5%).

STEP D:

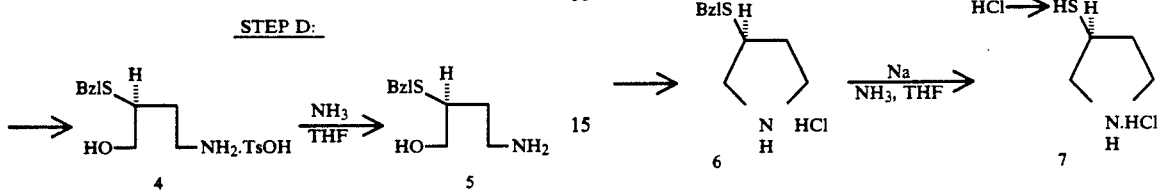

(S)-4-Amino-2-benzylthio-1-butanol (5)

Gaseous NH₃ was bubbled through a suspension of amine salt 4 (55.3 g, 0.144 mol) in anhydrous THF (600 ml) for ca. 15 minutes. The mixture was filtered to remove NH₄OTs and the filtrate was evaporated i.v. to give the free amine 5 (31.8 g) as an oil.

STEP E:

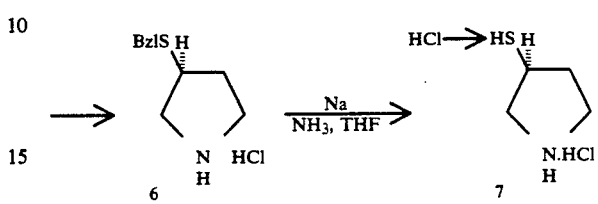

(S)-3-Benzylthiopyrrolidine hydrochloride (6)

Diisopropyl azodicarboxylate (39.6 ml, 0.301 mol) was added to a solution of triphenyl phosphine (88.8 g, 0.339 mol) in anhydrous THF (600 ml). The solution was briefly cooled in an ice-bath then stirred at RT under a N₂ atmosphere for ca. 10 minutes. A thick slurry formed. The mixture was treated with a solution of the amino alcohol 5 (31.8 g, 0.150 mol) in THF (25 ml) and stirred at room temperature for 90 minutes to give a light tan solution. The solution was evaporated i.v. to a viscous oil which was dissolved in EtOAc (400 ml) and extracted with 1N HCl (250 ml, 2×125 ml). The aqueous extracts were washed with EtOAc (3×100 ml) and Et₂O (100 ml), evaporated i.v. to an oil, seeded, and left under high vacuum to provide compound 6 (29.44 g, 85%) as a tacky, yellow solid.

STEP F:

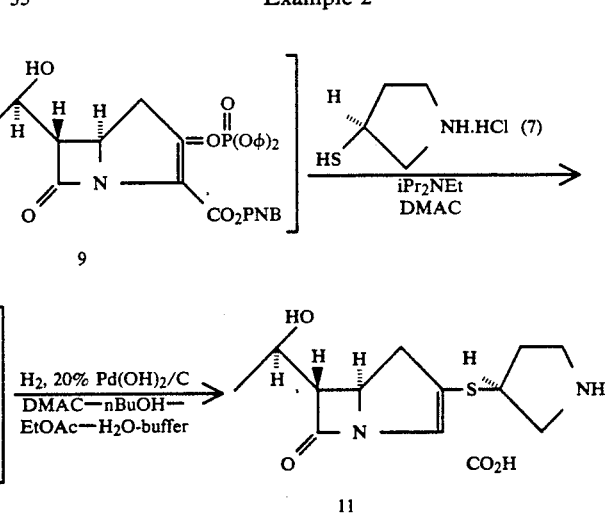

(S)-3-Mercaptopyrrolidine hydrochloride (7)

A solution of benzylthio pyrrolidine hydrochloride 6 (29.4 g, 0.128 mol) in anhydrous THF (20 ml) was added to a solution of sodium (12.5 g, 0.543 mol) in NH₃ (500 ml). The solution was stirred under a N₂ atmosphere for 15 minutes at dry ice-acetone temperature and for 15 minutes at ambient temperature. The resulting, blue solution was cautiously treated with absolute MeOH (30 ml) and evaporated i.v. to a semi-solid residue. This material was taken up in 6N HCl, filtered, and evaporated i.v. The resulting semi-solid residue was mixed with iPiOH (200 ml) and filtered to remove NaCl. The filtrate was evaporated i.v. to provide the mercapto pyrrolidine hydrochloride 7 (18.05 g) as a yellow, waxy solid.

Example 2'

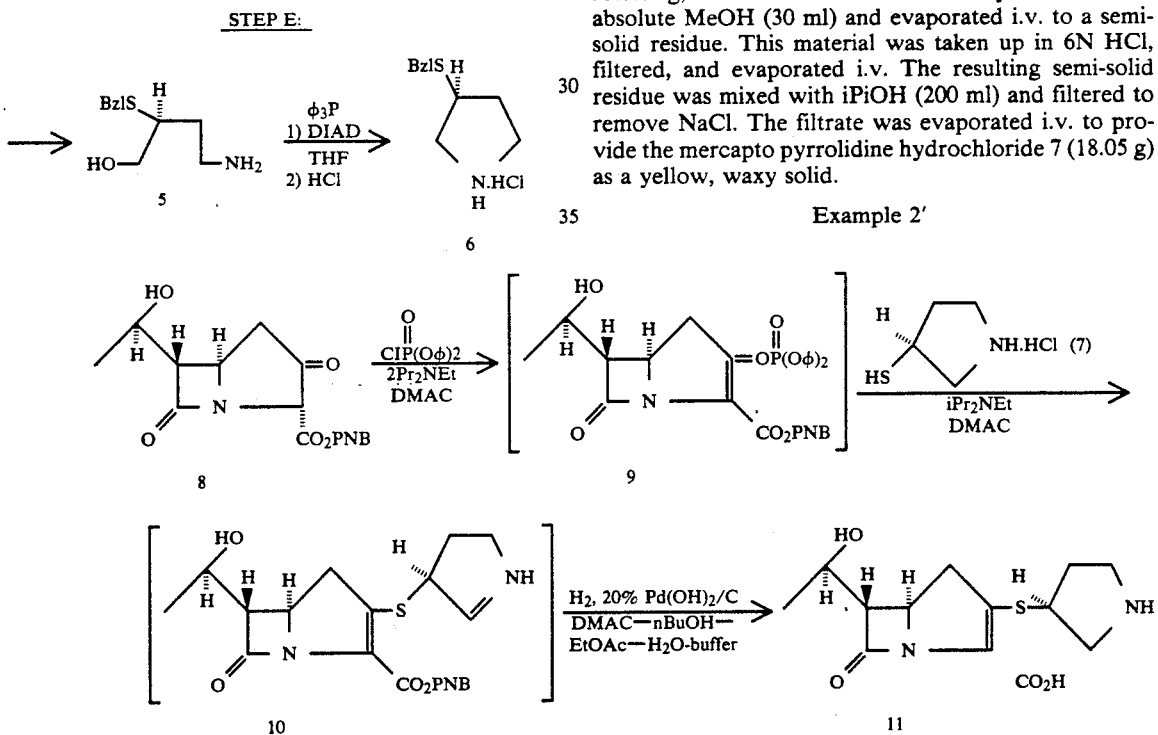

(5R, 6S)-6-[(R)-1-Hydroxyethyl]-2-[(S)-3-pyrrolidinylthio]-carbapen-2-em-3-carboxylic acid (11)

A solution of bicyclic keto ester 8 (200 mg, 0.60 mmol) in anhydrous dimethylacetamide (2.0 ml) was cooled in an ice-bath under a N₂ atmosphere and treated with diphenyl chlorophosphate (124 £1, 0.60 mmol) and iPi₂NEt (114 £1, 0.65 mmol). The resulting solution was stirred at ice-bath temperature for 20 minutes in order to complete the formation of the vinyl phosphate 9. The solution was treated with MeOH (25 £1) and iPr₂NEt (206 £1, 1.18 mmol), stirred at room temperature for 15 minutes, then cooled in an ice-MeOH bath to ca. −20° C. The mercapto amine hydrochloride 7 (84 mg, 0.60 mmol) was added and the reaction mixture was stirred at ca. −20° for 50 minutes to give a solution containing the addition product 0. A portion (1.0 ml) of this solution was hydrogenated as described below and the remainder was formimidoylated as described in the next example.

The reaction mixture aliquot (1.0 ml) was diluted with n-butanol (5.7 ml), EtOAc (2.9 ml), H₂O (5.7 ml) and 0.5M pH 6.8 N-methyl morpholinehydrochloric acid buffer (2.9 ml), treated with 20% Pd (OH)₂ on Darco G-60 (43 mg), and hydrogenated at 45 psi on a Parr shaker for 105 minutes. The mixture was filtered through a water washed cellite pad in order to remove the catalyst. The aqueous portion of the filtrate was washed with CH₂Cl₂ (2 × 10 ml), briefly evaporated i.v. to remove volatile organics, and charged onto a Dowex 50-X4 column (Na form, 200–400 mesh, 1.5 × 33 cm). The column was eluted with H₂O in a cold room; 7 ml fractions were collected every 2 minutes. Fractions 11–40 were combined, concentrated i.v., and lyophilized to give the derivative 11 (29.7 mg) as a fluffy, white solid.

Example 3'

(5R,6S)-6[(R)-1-Hydroxyethyl]-2-[(S)-N-formimidoyl-3-pyrrolidinylthio]carbapen-2-em-3-carboxylic acid (13)

The remainder of the reaction mixtu ⸱ from the preceding example that contained the crude ⸱ino ester 10 (0.287 mmol) was cooled in an ice-bath and treated with benzylformimidate hydrochloride (54 mg, 0.314 mmol) and iPr₂NEt (110 £1, 0.632 mmol). The reaction mixture was stirred at 5° C. under a N₂ atmosphere. After 20 minutes, additional benzylformimidate hydrochloride (81 mg, 0.472 mmol) and iPr₂NEt (165 £1, 0.948 mmol) were added and stirring with ice bath cooling was continued. The reaction mixture, which contains the foramidine ester 12, was diluted with n-BuOH (5.7 ml), EtOAc (2.9 ml), H₂O (5.7 ml) and 0.5M pH 6.8 N-methyl morpholinehydrochloric acid buffer (2.9 ml), treated with 20% Pd(OH)₂ on Darco G-60 (43 mg), and hydrogenated on a Parr shaker for 60 minutes at 45 psi. The mixture was filtered through a water-washed cellite pad to remove the catalyst which was washed with additional water. The aqueous portion of the filtrate was washed with CH₃Cl₂ (2 × 10 ml), briefly evaporated i.v., and charged onto a Dowex 50-4X column (Na form, 200–400 mesh, 1.5 × 33 cm). The column was eluted with H₂O in a cold room; 3 ml fractions were collected every 2 minutes. The product fractions were located by UV and HPLC. Fractions 15–25 were combined, concentrated i.v., and lyophilized to afford the formamidine 13 (17 mg) as a white, fluffy solid.

Example 4'

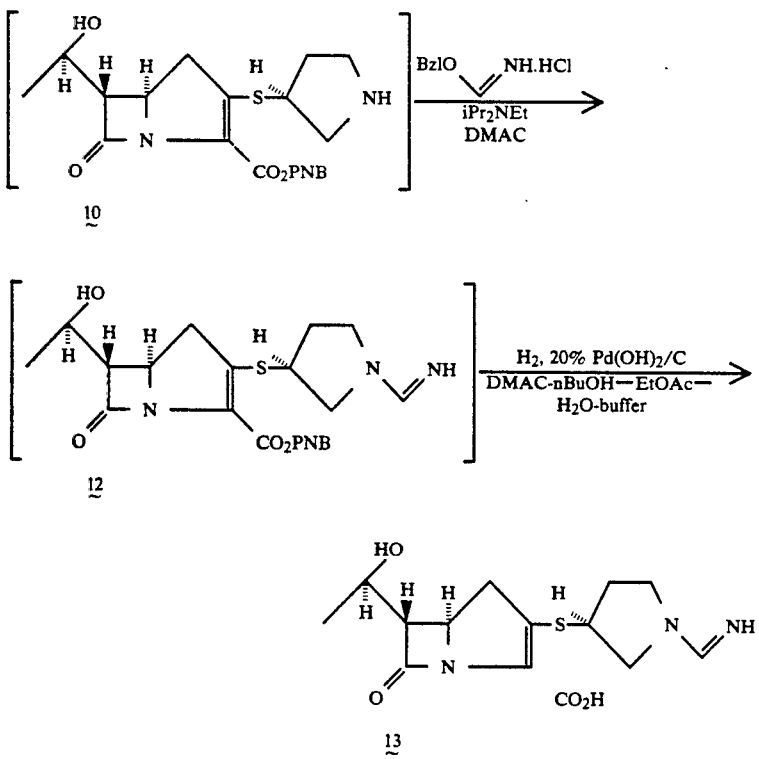

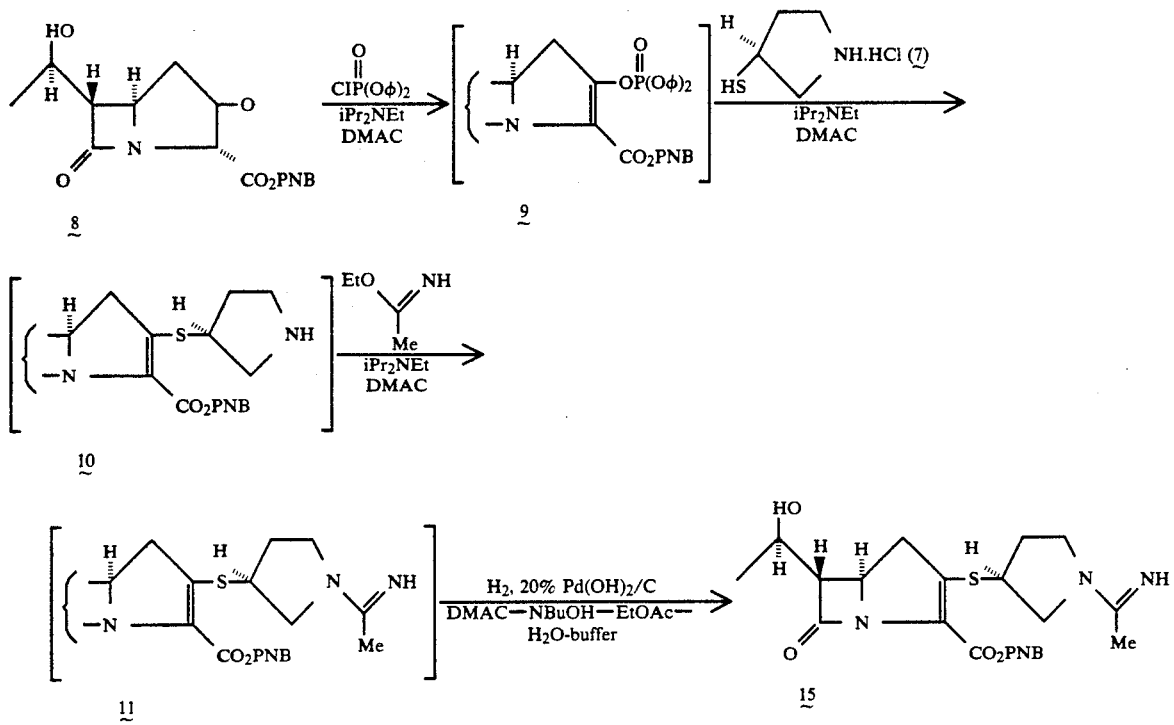

(5R,6S)-6-[(R)-1-Hydroxyethyl]-2-[(S)-N-Acetimidoyl-3-pyrrolidinylthio]carbapen-2-em-3-carboxylic acid (15)

A solution of bycyclic keto ester 3 (100 mg, 0.287 mmol) and diphenyl chlorophosphate (62 £1, 0.301 mmol) in anhydrous dimethyl acetamide (1.0 ml) was cooled in an ice-MeOH bath to ca −10° and treated with iPr₂NEt (57 £1, 0.327 mmol). The resulting solution was stirred under a N₂ atmosphere with ice-bath cooling for 20 minutes. The resulting solution of vinyl phosphate 9 was treated with MeOH (10 £1) and iPr₂NEt (103 £, 0.591 mmol), stirred at room temperature for 15 minutes, then cooled to ca. −20° C. The solution was treated with (S)-3-mercaptopyrrolidine hydrochloride (7) (42 mg, 0.301 mmol) and stirred between −20° C. and −10° C. for 45 minutes to give the addition product 10.

The reaction mixture was cooled in an ice-bath and treated with ethyl acetimidate hydrochloride (37 mg, 0.301 mmol) and iPr₂NEt (57 £1 0.301 mmol). After stirring for 35 minutes at ca. 5° C., the reaction mixture was treated with additional ethyl acetimidate hydrochloride (37 mg) and iPr₂NEt (57 £1) and stirred a further 35 minutes in the cold. The solution of crude 15 was diluted with n-BuOH (5.7 ml), EtOAc (2.9 ml), H₂O (5.7 ml), and 0.5M pH 6.8 N-methylmorpholinehydrochloric acid buffer (2.9 ml), treated with 20% Pd(OH)₂ on Darco G-60 (43 mg), and hydrogenated at 45 psi for 60 minutes on a Parr shaker. The mixture was filtered through a water washed cellite pad to remove the catalyst. the aqueous portion of the filtrate was separated, washed with two equal volumes of CH₂Cl₂, evaporated i.v. briefly, and chromatographed on a column of Dowex 50-X4 resin (Na form, 200–400 mesh, 1.5×33 cm) in a cold room. The column was eluted with H₂O at a flow rate of 13.6 ml fractions every 2.0 minutes. The fractions were assayed for product by U.V. Fractions 11–25 were combined, concentrated i.v., and lyophilized to provide the N-acetimidoyl derivative 15 (37 mg) as a white, fluffy solid.

Example 5'

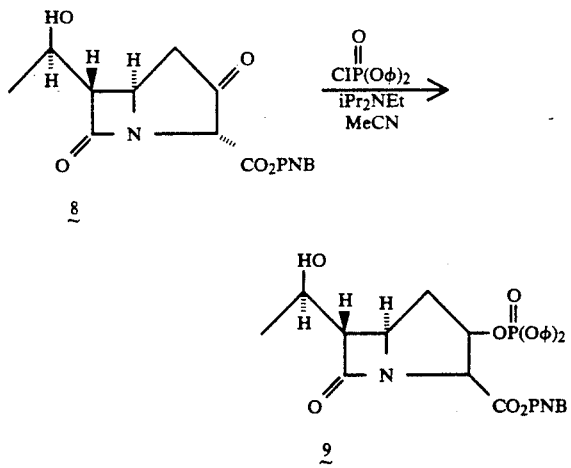

A solution of bicyclic keto ester 8 (1.393 g, 4 mmol) in anhyd MeOH (16 ml) was cooled in an ice-bath under a N₂ atmosphere and treated with iPr₂NEt (836 £1, 4.8 mmol) and CiPO (OO)₂ (870 £1, 4.2 mmol). The solution was stirred at 0° for 30 minutes, then diluted with EtOAc (100 ml), washed with H₂O (2×100 ml), 1M pH 3 buffer (50 ml), 5% NaHCO₃ (25 ml) and ine, dried with MgSO₄ and filtered. The filtrate was concentrated i.v. to ca. 5 ml, diluted with Et₂O (ca. 10 ml) and seeded. A copious white precipitate formed. The mixture was diluted with Et₂O and filtered. The solid was washed with Et₂O and dried i.v. to give the vinyl phosphate 9 (1.47 g, 63%) as an off-white solid.

Example 6'

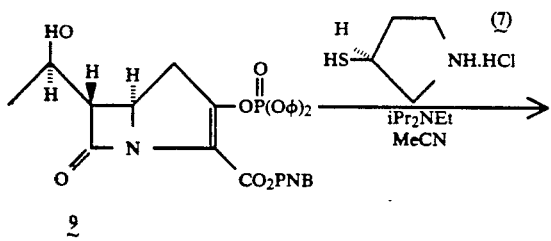

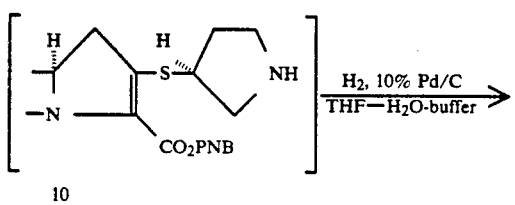

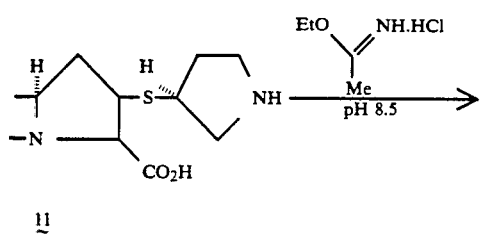

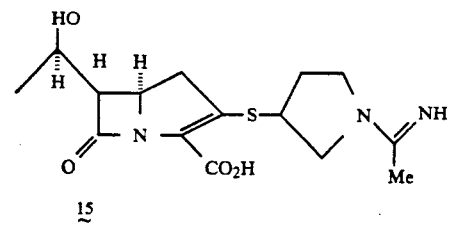

(5R,6S)-6-[(R)-1-Hydroxyethyl]-2-[(S)-N-acetimidoyl-3-pyrrolidinylthio]carbapen-2-em-3-carboxylic acid (15)

The bicyclic vinyl phosphate 9 (125 mg, 0.215 mmol) and (S)-3-mercapto pyrrolidine hydrochloride 7 (38 mg, 0.269 mmol) were dissolved in anhydrous MeOH (1.07 ml) under a ₂ atmosphere. The solution was cooled in an ice-bath, treated with iPr₂NEt (56 £1, 0.323 mmol), and stirred in the cold. After 12 minutes, the reaction mixture was treated with additional iPr₂NEt (10)11, 0.057 mmol) and stirred a further 8 minutes in the cold to complete the conversion to intermediate 10.

The reaction mixture was added to Et₂O (10 ml) and filtered through a cellite pad. The pad was then eluted with THF (17 ml)-H₂O (8 ml)-0.1M pH 7 phosphate buffer to remove the amino ester 10. The eluant was mixed with 10% Pd on charcoal (30 mg) and hydrogenated at 45 psi for 60 minutes on a Parr Shaker. The mixture was filtered and the filtrate was extracted with EtOAc (3×20 ml), evaporated i.v. to remove volatile organic solvents, and passed through a 0.45 £ Gelman acrodisc. U.v. analysis showed that the resulting solution (10 ml) contained the amino acid 10 (25.7 mg, 0.086 mmol).

The solution was cooled in an ice-bath with stirring, basified to pH 8.5 with 1N NaOH, and treated with ethyl acetimidate hydrochloride (500 mg). The pH was maintained at 8.5 with additional base. After 12 minutes and 21 minutes, additional portions (250 mg each) of ethyl acetimidate hydrochloride were added. After 30 minutes, the reaction mixture was brought to pH 7.0 with 2N HCl, concentrated i.v. to 6.5 ml, and added to a Dowex 50-X4 column (Na form, 200–400 mesh, 1.5×34 cm). The column was eluted with H₂O in a cold room; 5 ml fractions were collected every 2 minutes. The product containing fractions (40-66) were located by UV, concentrated i.v. to ca. 10 ml, and lyophilized to afford the acetimidoyl derivative 15 (16.1 mg) as a yellow, amorphous solid.

Example 7'

STEP A:

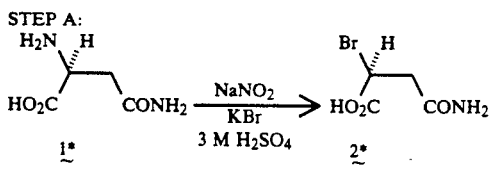

(S)-2-Bromo-3-carbamoylpropionic acid (2*)

L-Asparagine monohydrate 1* (37.5 g, 0.25 mol) was dissolved in 3M H₂SO₄ (330 ml) and treated with KBr (39.3 g, 0.75 mol). The solution was stirred and cooled in an ice-MeOH bath to ca. −10° C. Some precipitation occurred. A solution of NaNO₂ (21.6 g, 0.31 mol) in H₂O (38 ml) was added dropwise over 80 minutes. The internal temperature was kept at −10° to −5° during the addition and for 90 minutes afterward. The mixture was filtered and the solid portion washed with ice cold H₂O (3x) and dried overnight to give the product 2* (31.64 g, 65%) as an off-white solid: [α]$_D$= −67.8° (C 4.51, EtOH).

STEP B:

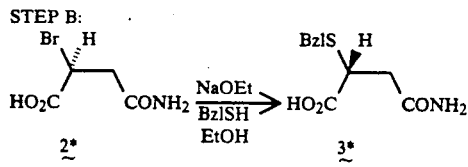

(R)-2-Benzylthio-3-carbamoylpropionic acid (3*)

Sodium (8.05 g. 0.35 mol) was dissolved in anhydrous EtOH (350 ml) under a N₂ atmosphere. The solution was cooled in an ice-bath and treated with BzlSH (46.7 ml, 0.398 mmol). After stirring 15 minutes at 0°, the solution was treated with bromo acid 2* (31.24 g, 0.159 mol) and then stirred at 0° for 1.5 hours. The mixture was concentrated i.v. The residue was partitioned between H₂O (400 ml) and Et₂O (400 ml, 2×200 ml). The aqueous phase was cooled in an ice bath and acidified to jpH 2.5 with concentrated HCl. The precipitate was collected, washed with H₂O (3×) and Et₂O (2×) and dried i.v. to a white solid (34.65 g, 91%0. [α]$_D$= +217.9° (c 2.02, MeOH). The crude product was dissolved in refluxing iPrOH (450 ml). After cooling to room temperature, the crystallized product was collected, washed with ice-cold iPrOH and Et₂O, and dried i.v. to give 3* as white needles (29.53 g, 77.6%): [α]$_D$= +219.1° (c 2.00, MeOH).

STEP C:

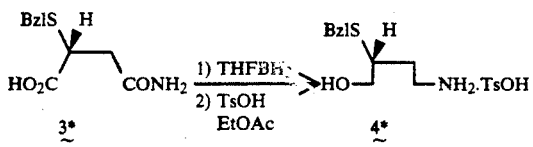

(R)-4-Amino-2-benzylthio-1-butanol p-toluene sulfonic acid salt (4*)

Amido acid 3* (15.00 g, 62.7 mmol) was suspended in anhydrous THF (100 ml) and stirred under a N₂ atm at room temperature. 1M BH₃ in THF (167 ml, 8 eq hydride) was added dropwise over 30 minutes. Gas evolved and solution was obtained. The resulting clear solution was heated at reflux for 6 hours, then stirred at room temperature overnight (15 hours). 6N HCl (30 ml) was added dropwise at room temperature and the mixture was heated to reflux and kept there for 15 minutes. After cooling to room temperature, the mixture was evaporated i.v. The residue was taken up in H₂O (100 ml) and EtOAc (100 ml) and stirred while adding 50% aqueous NaOH to pH 11. The layers were separated and the aqueous portion was extracted with more EtOAc (2×50 ml). The combined EtOAc solution was washed with brine, dried with MgSO₄, filtered, and evaporated i.v. to a slightly hazy oil (13.93 g). This material in EtOAc (50 ml) was added to a solution of TsOH·H₂O (11.93 g, 62.7 mmol) in EtOAc (150 ml). A small sample of the resulting solution was scratched and cooled to give a white precipitate. The precipitate was collected, washed with EtOAc and Et₂O, and dried i.v. to a white powder. The powder was added to the remainder of the solution to give a copious white precipitate. After storing in a refrigerator, the mixture was filtered to remove the precipitate which was then washed with a small portion of cold EtOAc and with EtiO. The filter cake was dried i.v. to give the product 4* (11.61 g, 48% as small white needles: [α]$_D$=+45.1° (c 2.03, MeOH).

STEP D:

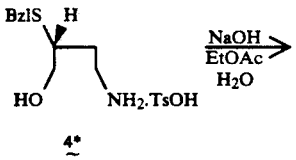

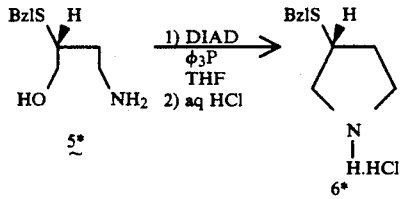

(R)-3-Benzylthiopyrrolidine Hydrochloride (6*)

Amine salt 4* (5.75 g, 0.015 mol) in H₂O (100 ml) was treated with 1N NaOH (30 ml, 0.03 mol) and extracted with EtOAc (100 ml, 3×50 ml). The combined extracts were washed with brine, dried with MgSO₄, filtered, and evaporated i.v. to give (R)-4-amino-2-benzylthio-1-butanol (5*) (2.93 g, 92%) as a clear oil.

DIAD (3.65 ml, 27.7 mmol) was added to a solution of φ₃P (8.00 g, 30.5 mmol) in anhydrous THF (70 ml). The solution was stirred at room temperature under a N₂ atm for 15 minutes during which time a white precipitate formed. A solution of the amine alcohol 5* (2.93 g, 13.87 mmol) in anhydrous THF (15 ml) was added and the mixture was stirred at room temperature and under N₂ overnight (15.5 hours). The mixture gradually gave a yellow solution. Water (1 ml) was added and the solution was stirred a few minutes to destroy excess DIAD. 2.5N HCl (30 ) was added and the solution was evaporated i.v. The residue was partitioned between H₂O (50 ml) and EtOAc (50 ml). The aqueous portion was washed with EtOAc (3×50 ml) and Et₂O (2r50nil) and evaporated i.v. The residue was stripped with CH₂Cl₂, then taken up in CH₂Cl₂, dried with MgSO₄, filtered and evaporated i.v. to a clear, viscous gum (2.23 g). This material was triturated with Et₂O (3×) and dried i.v. to give the pyrrolidine hydrochloride 6* (2.13 g, 67%) as a hygroscopic white solid.

STEP E:

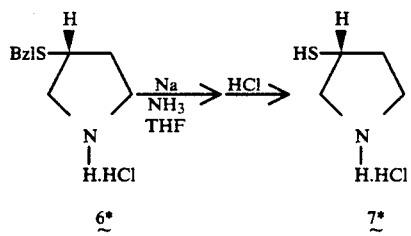

(R)-3-Mercaptopyrrolidine hydrochloride (7*)

Liquid NH₃ (50 ml) was condensed in a 3-neck, 250 ml RB flask fitted with a magnetic stirrer, gas inlet tube, rubber septum, and dry ice condensor. The flask was cooled in a dry ice-acetone bath to facilitate the NH₃ condensation sodium metal (0.91 g, 39.57 mmol) was added and the mixture was stirred at ambient temperature to give a deep blue solution. A thin suspension of the amine hydrochloride 6* (2.13 g, 9.27 mmol) in anhydrous THF (3×5 ml) was added and the resulting solution was stirred at ambient temperature for 30 minutes. Solid NH₄Cl (1.6 g, 30 mmol) was cautiously added to the reaction mixture to dispel the blue color. The NH₃ was evaporated i.v. to give a residue which was taken up in H₂O (35 ml) containing 1N HCl (15 ml). The aqueous solution was washed with Et₂O (2×50 ml) and evaporated i.v. to a solid which was triturated with iPrOH (10 ml, 2×5 ml) and filtered. The filtrate was evaporated i.v. to a clear, viscous oil (1.33 g). This material was triturated with Et₂O (3×) and stripped i.v. With abs MeOH and with toluene (2×) to give the product 7* (1.18 g, 91%) as a clear, viscous gum.

EXAMPLE 8'

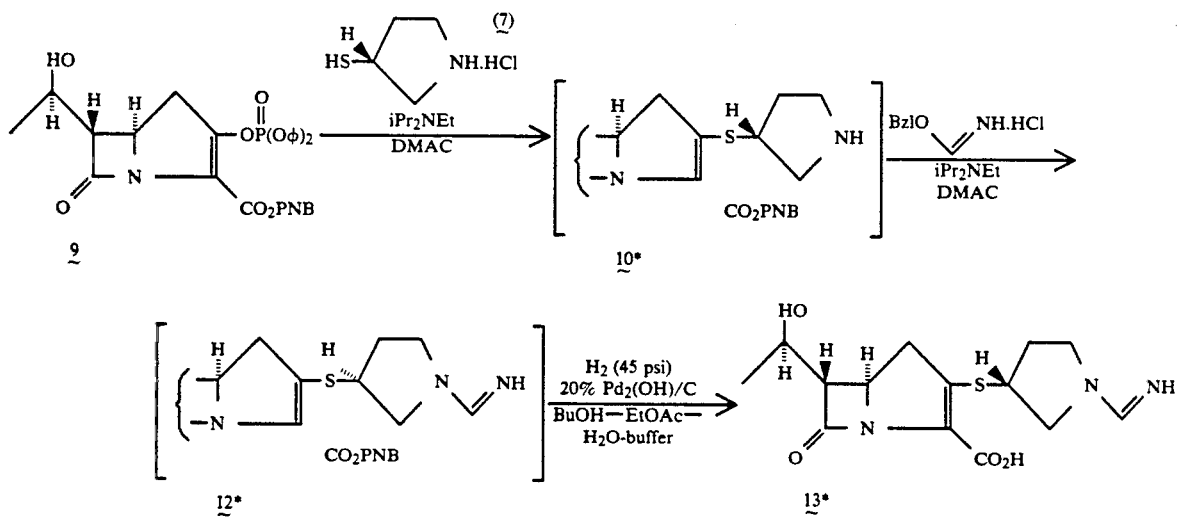

(5R,6S)-6-[(R)-1-Hydroxyethyl]-2-[(R)-N-Formimidoyl-3-pyrrolidinylthio]-carbapen-2-em-3-carboxylic acid (13*)

Vinyl phosphate 8* (116 mg, 0.2 mmol) and amine hydrochloride 7* (30.7 mg, 0.22 mmol) were dissolved in anhydrous dimethyl acetamide (0.7 ml) under a $N_2$ atm. The solution was cooled in a dry ice-MeOH bath at ca. −20° while iPr₂NEt (77 £1, 0.44 mmol) was added. The resulting solution was stirred at −20° to −15° for 45 minutes to give 10*, then treated with benzyl formimidate hydrochloride (37.7 mg 0.22 mmol) and iPr₂-NEt (40 £1, 0.23 mmol). The resulting viscous reaction mixture was stirred in an ice bath for 90 minutes. The mixture containing 12* was diluted with n-BuOH (4 ml), EtOAc (2 ml), $H_2O$ (4 ml), and 0.5M pH 6.8 N-methyl morpholine-hydrochloric acid buffer (2 ml), treated with 20% Pd (OH)₂ on Darco G-60 (30 mg), and hydrogenated on a Parr shaker at 45 psi for 60 minutes. The mixture was filtered through a water washed pad of cellite. The aqueous portion of the filtrate was separated, washed 3× with $CH_2Cl_2$, and evaporated i.v. to remove volatile organism. The aqueous solution was charged onto a column of Dowex 50×4 (1.5 cm dia×33.5 cm. Na cycle, 200-400 mesh) which was eluted with DI $H_2O$ in a cold room, 8 ml fractions were collected every 2.2 minutes. The progress of the chromotography was monitored by UV. Fractions 22-31 were combined (83 ml), conc i.v. to ca. 30 ml and lyophilized to give the formamidine 13* (27 mg) as a white, amorphous powder.

Example 9'

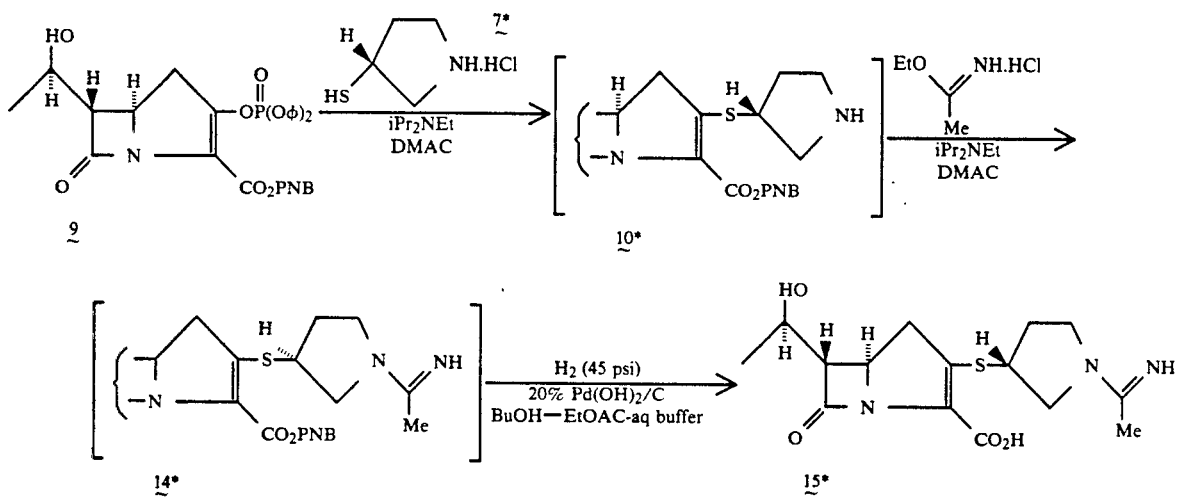

(5R,6S)-6-[(R)-1-Hydroxyethyl]-2-[(R)-N-Acetimidoyl-3-pyrrolidinylthio]-carbapen-2-em-3-carboxylic acid (15*)

Vinyl phosphate 9 (145 mg. 0.25 mmol) and amine hydrochloride 7* (38.4 mg, 0.275 mmol) were dissolved in anhydrous dimethylacetamide (0.875 ml) under a $N_2$ atm. The solution was cooled in a dry ice-MeOH bath at −20° and treated with iPr₂NEt (96 £1, 0.55 mmol). The resulting solution was stirred for 45 minutes at −20° to −15° to provide intermediate 10*, then treated with EtO—C(CH₃)=NH.HCl (34 mg, 0.275 mmol) and iPr₂NEt (50 £1, 0.287 mmol). The resulting mixture was stirred at 0° for 90 minutes to give intermediate 14*, then diluted with nBuOH (5 ml), EtOAc (2.5 ml), $H_2O$ (5 ml) and 0.5M pH 6.8 N-methylmorpholinehydrochloric acid buffer (2.5 ml). The mixture was treated with 20% Pd(OH)2 on Darco G-60 (38 mg) and hydrogenated at 45 psi for 1 hour. The mixture was filtered through a water washed super cell pad. The aqueous portion of the filtrate was washed with CH2Cl2 (2×) and evaporated i.v. to remove organus. The aqueous solution was charged onto a column of Dowex 50×4 resin (Na cycle, 200–400 mesh, 1.5 cm×33 cm) which was eluted with DI H2O in a cold room. 8 ml fractions were collected every 2.2 minutes. The progress of the purification was followed by UV spectroscopy. Fractions 18–30 were combined (112 ml), concentrated i.v. to ca 20 ml and lyophilized to give the autimidoyl derivative 15* (45 mg) as a white, amorphous powder.

Example 9'A

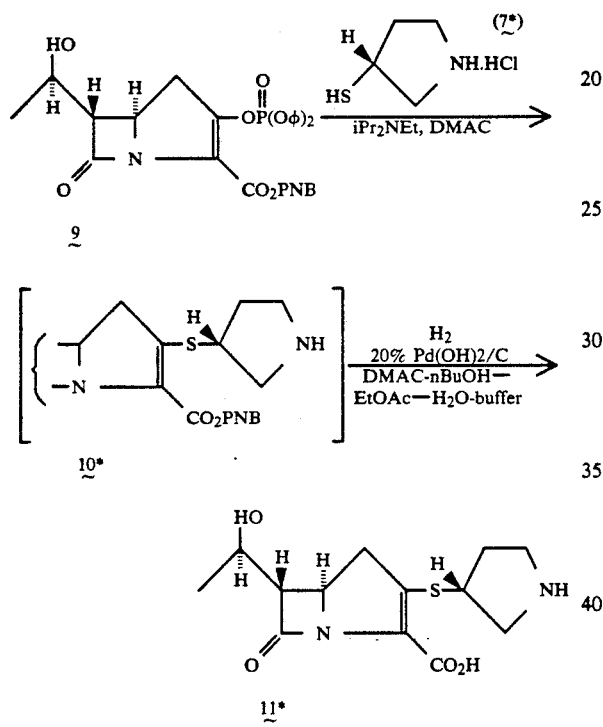

(5R,6S)-6-[(R)-1-Hydroxyethyl]-2-[(R)-3-pyrrolidinyl-thio]-carbapen-2-em-3-carboxylic acid (11*)

A solution of vinyl phosphate 9 (116 mg, 0.2 mmol) and mercaptoamine hydrochloride 7* (30.7 mg, 0.22 mmol) in anhydrous dimethylacetamide (0.7 ml) was cooled in a dry ice-MeOH bath at ca. −20° and stirred under a N2 atmosphere. The solution was treated with N,N-diisopropylethylamine (77 £1, 0.44 mmol) and stirred at −20° to −15° for 45 minutes to give the addition product 10*.

The reaction mixture containing 10* was diluted with n-butanol (5 ml), EtOAc (2.5 ml), H2O (5 ml), and 0.5M pH 6.8 N-methylmorpholine hydrochloric acid buffer (2.5 ml), treated with 20% Pd(OH)2 on Darco G-60 (30 mg), and hydrogenated at 45 psi for 60 minutes on a Parr shaker. The mixture was filtered through a water-washed supercell pad to remove the catalyst. The aqueous portion of the filtrate was washed with CH2Cl2, evaporated i.v. to remove volatile organics, and charged onto a column of Dowex 50-X4 resin (Na form, 200–400 mesh, 1.5×33 cm). The column was eluted with H2O in a cold room at the rate of 15 ml fractions every 4.8 minutes. On the basis of UV, fractions 6–12 were combined, concentrated i.v. to ca. 20 ml volume, and lyophilized to afford 11* (29 mg) as an off-white, amorphous solid.

Example 10'

Step A: 3-(1-p-Nitrobenzyloxycarbonyl)pyrrolidinol (17)

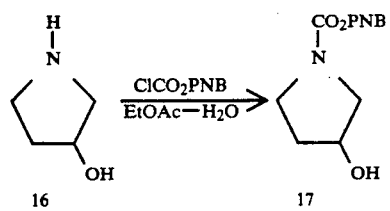

To a stirred mixture of 3-pyrrolidinol 16 (1.0 g, 11.5 mmol), EtOAc (20 ml) and water (20 ml) was added a solution of ClCO2PNB (1.240 g, 5.74 mmol) in EtOAc (30 ml) at 0°. After stirring for 50 minutes, the organic layer was washed with water (30 ml) and brine (10 ml), dried over MgSO4 and concentrated. The residue was chromatographed on silica gel using CHCl3—MeOH (400:1) to afford 17 (1.147 g, 75%) as a pale yellow powder.

Step B:
1-p-Nitrobenzyloxycarbonyl-3-p-toluenesulfonyloxypyrrolidine (18)

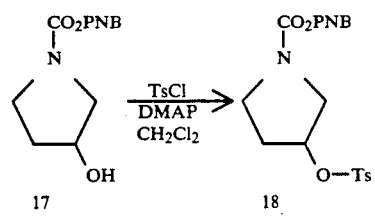

A mixture of 17 (340 mg, 1.28 mmol), 4-dimethylamino pyridine (234 mg, 1.92 mmol) and p-toluenesulfonyl chloride (365 mg, 1.87 mmol) in CH2Cl2 (10 ml) was stirred for 14 hours at room temperature under argon. The reaction mixture was diluted with EtOAc, washed with 5% NaHCO3 (50 ml), water (30 ml and brine, dried over MgSO4 and concentrated. The residue was chromatographed on silica gel using benzene-EtOAc (200:1) to give 18 (507 mg, 94%) as a caramel.

Step C:
1-p-Nitrobenzyloxycarbonyl-3-benzoylthiopyrrolidine (19)

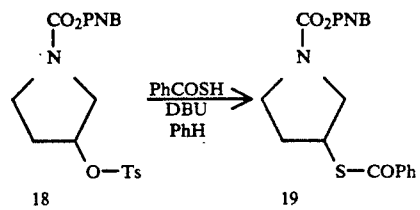

To a stirred solution of 18 (507 mg, 1.2 mmol) and PhCOSH (200 mg, 1.45 mmol) in benzene (20 ml) was added DBU (238 mg, 1.56 mmol) at room temperature.

After stirring for 3 hours at 80°, the reaction mixture was diluted with benzene (60 ml), then washed with saturated NaHCO$_3$ and brine, dried over MgSO$_4$. Evaporation of the solvent gave a residue, which was chromatographed on silica gel using benzene-EtOAc (97:3) to afford 19 (320 mg, 68.7%) as a pale yellow powder.

Step D:
1-p-Nitrobenzyloxycarbonyl-3-mercaptopyrrolidine (20)

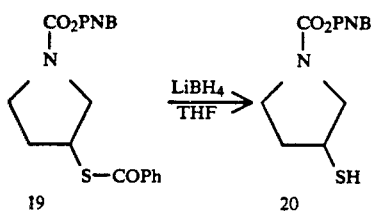

To a stirred solution of 19 (320 mg, 0.83 mmol) in THF (10 ml) was added LiBH$_4$ (150 mg, 6.8 mmol) at 0° under argon. After stirring for 1 hour at room temperature, the reaction mixture was acidified with 5% HCl and diluted with EtOAc (100 ml), then washed with water and brine, and dried over MgSO$_4$. Removal of the solvent gave a residue, which was chromatographed on silica gel using benzene-EtOAc (93:7) to give 20 (100 mg, 42.9%) as a powder.

EXAMPLE 11' p-Nitrobenzyl (5R,6S)-6-[(R)-1-hydroxyethyl]-2-[(R,S)-N-(p-nitrobenzyloxycarbonyl)-3-pyrrolidinylthio]-carbapen-2-em-3-carboxylate (21)

A solution of vinyl phosphate 9 (275 mg, 0.473 mmol) and mercaptan 20 (147 mg, 0.521 mmol) in anhydrous MeOH (1.5 ml) was cooled in an ice-bath and treated with iPr$_2$NEt (91 £1, 0.52 mmol). The resulting solution was stirred under a N$_2$ atmosphere at ca. 5° C. for 90 minutes, then diluted with EtOAc (30 ml), washed with H$_2$O, saturated aqueous NaHCO$_3$ and brine, dried with MgSO$_4$, filtered, and evaporated i.v. to a foam. The crude product was chromatographed on three 1 mm×20×20 cm silica gel GF plates using 9:1 EtOAc-cyclohexane as developing solvent to afford the diastereomeric product mixture 21 (256 mg, 88%) as a pale yellow solid after lyophilization from dioxane.

EXAMPLE 12'

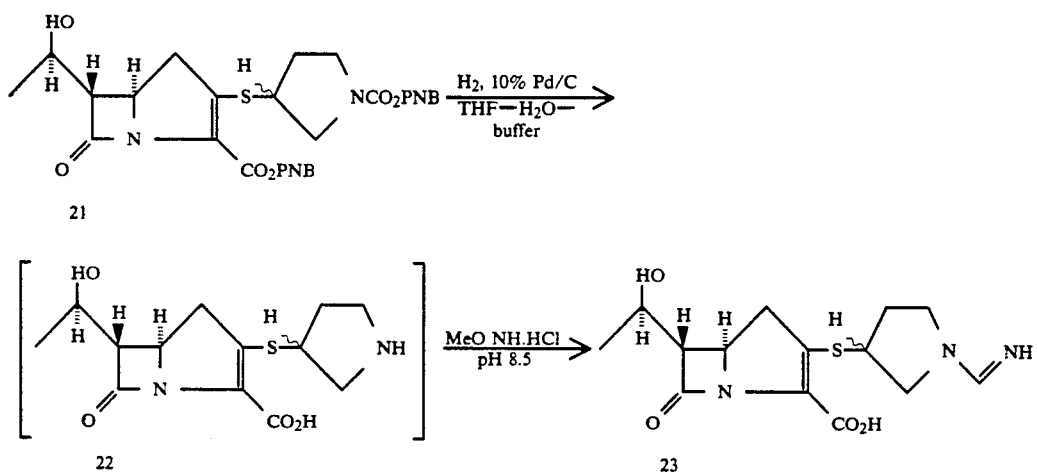

(5R,6S)-6-[(R)-1-Hydroxyethyl]-2-[(R,S)-N-formimidoyl-3-pyrrolidinylthio]-carbapen-2-em-3-carboxylic acid (23)

A solution of bis protected derivative 21 (125 mg, 0.204 mmol) in THF (7.7 ml) was diluted with H$_2$O (4.2 ml) and 0.1M pH7 phosphate buffer (2.1 ml), treated with 10% Pd/C (25 mg), and hydrogenated on a Parr shaker at 45 psi for 3 hours. The mixture was diluted with H$_2$O (10 ml) and filtered. The filtrate was washed with Et$_2$O (2×15 ml), evaporated i.v. to remove volatile organus, and filtered through a 0.45 £ filter disc. UV analysis of the resulting solution showed that it contained 28.3 mg (46%) of the amine acid 22.

The amine acid solution was stirred in an ice-bath, brought to pH 8.5 with 2.5N NaOH, and treated with

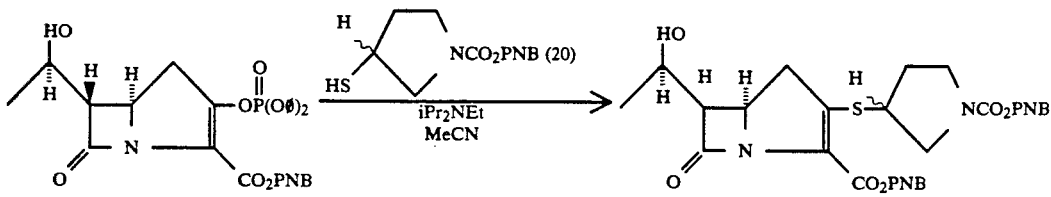

methyl formimidate hydrochloride (400 mg). After 15 minutes, a second portion of methyl formimidate hydrochloride (400 mg) was added. The pH was maintained at 8.5 by addition of 2.5N NaOH. After 30 minutes, the reaction mixture was acidified to pH 7.0 with 3N HCl, washed with EtOAc, and concentrated i.v. to ca. 7 ml. The solution was charged onto a column of Dowex 50×4 resin (Na form, 200-400 mesh, 1.5×31 cm) which was eluted with H₂O in a cold room; 4.4 ml fractions were collected every 2 minutes. The progress of the chromatography was followed by UV. Fractions 35–60 were combined, concentrated i.v. to ca. 10 ml, and lyophilized to provide the diastereomeric N-formimidoyl derivatives 23 (11 mg) as an off-white, amorphous solid.

EXAMPLE 13'

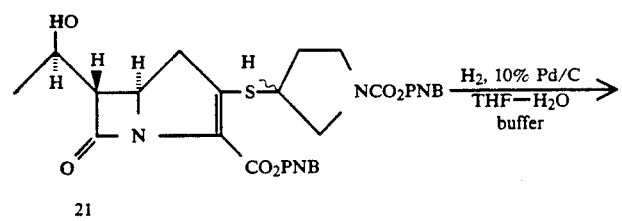

21

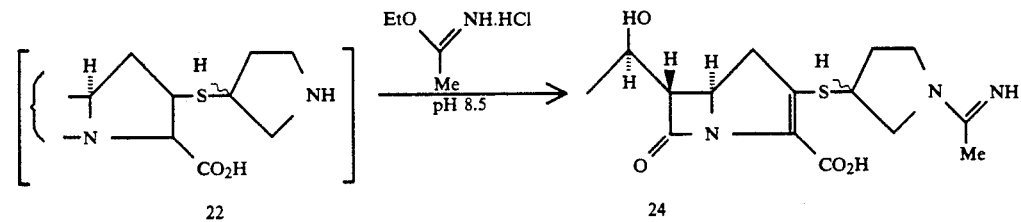

22                                          24

(5R,6S)-6-[(R)-1-Hydroxyethyl]-2-[(R,S)-N-acetimidoyl-3-pyrrolidinylthio]-carbapen-2-em-3-carboxylic acid (24)

A solution of bis protected derivative 21 (178 mg, 0.291 mmol) in THF (11 ml) was diluted with H₂O (6 ml) and 0.1M pH 7 phosphate buffer (3 ml), treated with 10% Pd/C (35 mg), and hydrogenated on a Parr Shaker at 45 psi for 3.5 hours. The mixture was diluted with H₂O (10 ml), filtered, extracted with EtOAc (2×15 ml), and evaporated i.v. to remove volatile organics UV analysis of the resulting solution (19.5 ml) showed that it contained 40 mg (46% yield) of the amino acid 22.

The amino acid solution was stirred in an ice-bath, adjusted to pH 8.5 with 2.5N NaOH, and treated with ethyl acetimidate hydrochloride (0.90 g). After 10 minutes, additional imidate hydrochloride (0.50 g) was added. The pH of the reaction mixture was kept at 8.5 by the addition of 2.5 NaOH. After stirring in the cold for 30 minutes, the reaction mixture was acidified to pH 7.0 and extracted with EtOAc (2×10 ml). The aqueous phase was concentrated i.v. to ca. 5 ml and applied to a column of Dowex 50-X4 (Na form, 200-400 mesh, 1.5×31 cm) which was eluted with H₂O in a cold room (5.5 ml fractions every 2 minutes). The product was located by UV analysis. Fractions 27–50 were combined, concentrated i.v. to ca. 20 ml, and lyophilized to afford the diastereomeric acetimidoyl derivatives 24 (18 mg) as an off-white, amorphous solid.

EXAMPLE 14'

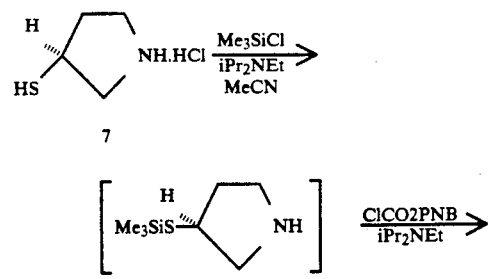

7

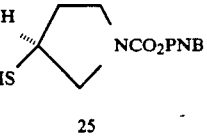

25

(S)-N-(p-Nitrobenzyloxycarbonyl)-3-mercaptopyrrolidine (25)

A suspension of mercaptoamine hydrochloride 7 (589 mg, 4.22 mmol) in anhydrous MeCN (3.2 ml) was stirred under a N₂ atmosphere with ice-bath cooling. The mixture was treated with N,N-diisopropylethylamine (1.69 ml, 9.71 mmol), stirred 5 min, and treated with chlorotrimethyl silane (0.70 ml, 5.52 mmol). After stirring 10 more minutes in the cold, the mixture was treated with a solution of p-nitrobenzyl chloroformate (910 mg, 4.22 mmol) in MeCN (1.0 ml) followed by more N,N-diisopropylethylamine (0.74 ml, 4.25 mmol). The resulting mixture was stirred in the cold for 15 minutes and at room temperature for 1 hour. The reaction mixture was diluted with EtOAc, washed with H₂O, 1N HCl, 5% aqueous NaHCO₃ and brine, dried with MgSO₄, filtered, and evaporated (i.v.) to a yellow gum. The crude product was chromatographed on EM silica gel 60 (60 g) using 25:1 CH₂Cl₂—EtOAc as eluting solvent to afford derivative 25 (858 mg, 72%) as a pale yellow oil.

EXAMPLE 15'

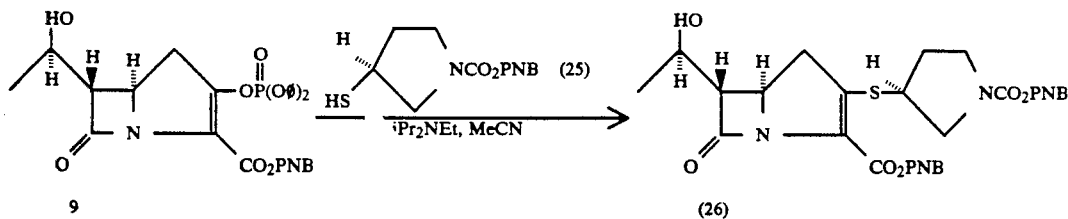

9                                              (26)

p-Nitrobenzyl(5R,6S)-6-[(R)-1-hydroxyethyl]-2-[(S)-N-p-nitrobenzyloxycarbonyl)-3-pyrrolidinylthio]-carbapen-2-em-3-carboxylate (26)

A solution of mercaptan 25 (105.5 mg, 0.37 mmol) and vinyl phosphate 9 (197.2 mg, 0.34 mmol) in anhydrous MeCN (1.36 ml) was cooled in an ice bath under a $N_2$ atmosphere and treated with N,N-diisopropylethylamine (71 1, 0.41 mmol). The resulting mixture was stirred in the cold for 75 minutes during which time a precipitate formed. The mixture was diluted with $CH_2Cl_2$ (40 ml), washed with $H_2O$, pH 3 buffer, 5% aqueous $NaHCO_3$, and brine, dried with $MgSO_4$, filtered, and evaporated i.v. to a pale yellow solid (225 mg). The crude product was triturated with several portions of ethyl ether to afford compound 26 (188 mg, 90%) as a pale yellow powder.

EXAMPLE 16'

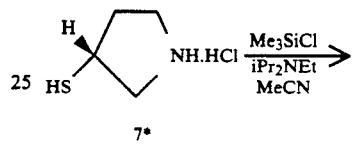

15

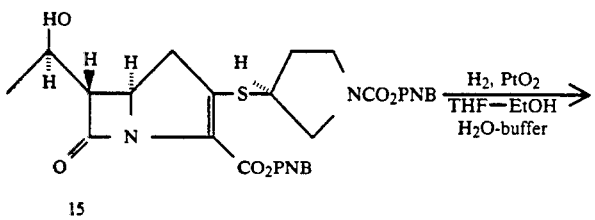

11

(5R,6S)-6-[(R)-1-Hydroxyethyl]-2-[(S)-N-acetimidoyl-3-pyrrolidinylthio]-carbapen-2-em-3-carboxylic acid (15)

A thin suspension of bis protected derivative 26 (30.6 mg. 0.05 mmol) in THF (3.6 ml), EtOH (1.8 ml), $H_2O$ (1.3 ml), and 0.1M pH 7.0 MOPS-NaOH buffer (1.5 ml) was added to a prereduced mixture of $PtO_2$ (30 mg) in EtOH (1.8 ml). The resulting mixture was vigorously stirred under an atmosphere of $H_2$ for 4.25 hours at room temperature, then filtered through a waterwashed pad of super cell to remove the catalyst. The filtrate was washed with EtOAc and 1:1 $EtOAc-Et_2O$, and concentrated i.v. to ca. 2 ml volume to give a solution containing compound 11.

The solution of crude 11 was cooled in an ice-bath, brought to pH 8.4 with 1N NaOH, stirred, and treated with ethyl acetimidate hydrochloride (124 mg, 1 mmol) in 8 portions over 45 min. The pH of the reaction mixture was maintained at 8.2–8.4 by addition of 1N NaOH.

After stirring an additional 15 minutes in the cold, the reaction mixture was acidified to pH 7 with 1N HCl and charged onto a column of Dianion HP-20 AG resin (50 ml). The column was eluted in a cold room first with water and then 5% $THF/H_2O$. The product fractions were located by UV in the 5% $THF/H_2O$ eluant, combined, concentrated i.v., and lyophilized to afford derivative 15 (10.6 mg) as an off-white, amorphous, solid.

EXAMPLE 17'

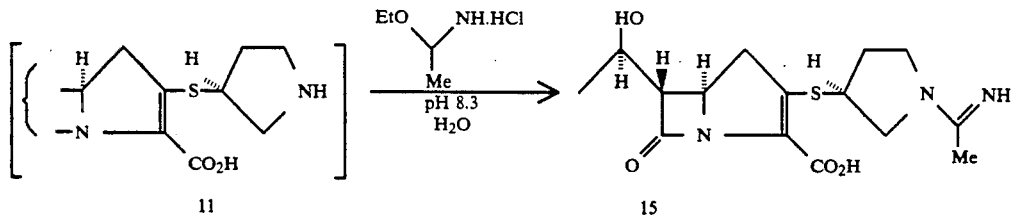

7*

25*

(R)-N-(p-Nitrobenzyloxycarbonyl)-3-mercaptopyrrolidine (25*)

N,N-Diisopropylethylamine 496 £1, 2.85 mmol) was added to a suspension of mercaptoamine hydrochloride 7* (173 mg, 1.24 mmol) in anhydrous MeCN (0.93 ml) and the resulting mixture was stirred under a $N_2$ atmosphere with ice bath cooling for 5 minutes. Chloromethyl silane (204 £1, 1.61 mmol) was added and the mixture was stirred at 0° for 10 minutes. A solution of p-nitrobenzyl chloroformate (267 mg, 1.24 mmol) in MeCN (0.31 ml) and more N,N-diisopropylethylamine (216 £1, 1.24 mmol) were added and the resulting mixture was stirred at 0° for 30 minutes and at room temperature for 60 minutes. The mixture was diluted with EtOAc, washed with H₂O, 1N HCl, 5% aq. NaHCO₃, and brine, dried with MgSO₄, filtered and evaporated i.v., to a pale yellow oil. The crude product was chromatographed on a EM silica gel 60 column (20 g) that was eluted with 2:1 hexane-ethyl acetate at a rate of 8 ml fractions/3.5 minutes. Fractions 16-22 gave the product 25* (198 mg) as a pale yellow oil which crystallized to an off-white solid on storage in a refrigeration.

EXAMPLE 18'

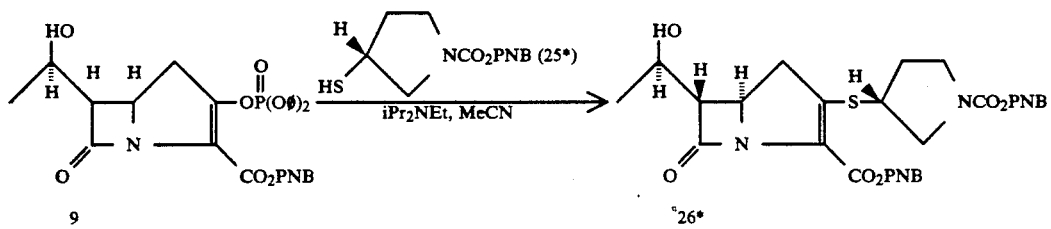

p-Nitrobenzyl (5R,6S)-6-[(R)-1-hydroxyethyl]-2-[(R)-N-(p-nitrobenzyloxycarbonyl)-3-pyrrolidinylthio]-carbapen-2-em-3-carboxylate (26*)

A solution of mercaptan 25* (29.1 mg, 0.103 mmol) and vinyl phosphate 9 (56.9 mg, 0.098 mmol) in anhydrous MeCN (0.4 ml) was cooled in an ice bath and stirred under a N₂ atmosphere. The solution was treated with N,N-diisopropylethylamine (18.8 μl, 0.108 mmol) and stirred in the cold. After ca. 30 minutes, a precipitate formed. After 60 minutes, the mixture was diluted with ice-cold MeCN (1 ml) and filtered. The filter cake was washed with several portions of EtOAc and dried i.v. to yield derivative 26* (14.3 mg) as an off-white solid.

Claims to the invention follow.
What is claimed is:

1. An antibacterial composition comprising a combination of a carbapenem having the following structure:

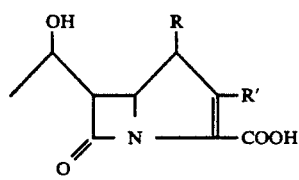

wherein
R is hydrogen or methyl, and
R' is

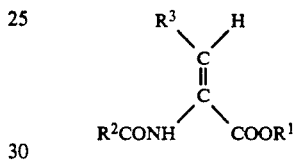

wherein
M is CH₃ or H;
and the easily removable pharmaceutically acceptable salt or ester derivatives thereof; and a dipeptidase (E.C.3.4.13.11) inhibitor, of the following structure, $$\begin{array}{c} R^3 \quad H \\ \diagdown \diagup \\ C \\ \parallel \\ C \\ \diagup \diagdown \\ R^2CONH \quad COOR^1 \end{array}$$

wherein
R² and R³ are hydrocarbon radicals in the range respectively of 3-10 and 1-15 carbon atoms; in either of these hydrocarbon radicals R² and R³, up to 6 hydrogens may be replaced by halogens, or a non-terminal methylene may be replaced by oxygen or sulphur, including oxidized forms of the latter; a terminal hydrogen in R³ can also be replaced by a hydroxyl or thiol group, which may be acylated, such as with an alkanoyl acid of 1-8 carbon atoms, or carbamoylated, including alkyl and dialkyl carbamate derivatives; or the hydrogen can be replaced by an amino group, which may be derivatized as in an acylamino, ureido, amidino, guanidino, or alkyl or substituted alkyl amino group, including quaternary nitrogen groupings; or, alternatively, there may be replacement by acid groups such as carboxylic, phosphonic or sulfonic acid groups or esters or amides thereof, as well as cyano; or combinations thereof, such as a terminal amino acid grouping; the ratio of the carbapenem to the dipeptidase inhibitor being within in the range of about 1:3 to 30:1.

2. The composition of claim 1 in which the combination is mixed with a pharmaceutical carrier.

3. The composition of claim 2 in which the carrier is adapted for injection.

4. The composition of claim 1 in which the carbapenem is 2-(1-acetimidoyl-pyrollidin-3-yl-thio)-6-(1-hydroxyethyl)-carbapen-2-em-3-carboxylic acid or sodium carboxylate.

5. The composition of claim 4 wherein the dipeptidase inhibitor is Z-7-(L-amino-carboxyethylthio)-2-(2,2-dimethylcyclopropane carboxamido)-2-heptanoic acid.

* * * * *